(12) United States Patent
Jacobs, Jr. et al.

(10) Patent No.: US 7,939,089 B2
(45) Date of Patent: May 10, 2011

(54) ATTENUATED MYCOBACTERIA AS VECTORS FOR GENE DELIVERY TO MAMMALIAN CELLS

(75) Inventors: William R. Jacobs, Jr., Pelham, NY (US); Glenn J. Fennelly, New York, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 572 days.

(21) Appl. No.: 11/794,372

(22) PCT Filed: Jan. 12, 2006

(86) PCT No.: PCT/US2006/001130
§ 371 (c)(1),
(2), (4) Date: Feb. 12, 2008

(87) PCT Pub. No.: WO2006/076517
PCT Pub. Date: Jul. 20, 2006

(65) Prior Publication Data
US 2008/0268541 A1    Oct. 30, 2008

Related U.S. Application Data

(60) Provisional application No. 60/643,535, filed on Jan. 12, 2005.

(51) Int. Cl.
*A61K 39/40* (2006.01)
*A61K 39/02* (2006.01)
*A61K 39/00* (2006.01)

(52) U.S. Cl. .................. 424/248.1; 536/23.1; 536/23.7; 424/93.1; 424/93.2; 424/93.21; 424/184.1; 424/200.1; 424/234.1

(58) Field of Classification Search ............... 424/184.1, 424/200.1, 203.1, 234.1, 248.1, 93.1, 93.2, 424/93.21; 536/23.1, 23.7
See application file for complete search history.

(56) References Cited

U.S. PATENT DOCUMENTS 5,783,386 A   7/1998  Jacobs, Jr. et al.
5,877,159 A * 3/1999  Powell et al. ............... 514/44 R

* cited by examiner

*Primary Examiner* — Rodney P. Swartz
(74) *Attorney, Agent, or Firm* — Amster, Rothstein & Ebenstein LLP

(57) ABSTRACT

Provided are mycobacteria comprising a recombinant gene operably liked to a mammalian promoter that directs expression of the recombinant gene from a mammalian cell. Also provided are mammalian cells comprising the above mycobacteria. Additionally provided are mycobacterial plasmids capable of replication in a mycobacterium. Further provided are methods of expressing a recombinant gene in a mammalian cell.

31 Claims, 15 Drawing Sheets

FL1-H: GFP

ATTENUATED MYCOBACTERIA AS VECTORS FOR GENE DELIVERY TO MAMMALIAN CELLS

CROSS-REFERENCE TO RELATED APPLICATION

This is a U.S. national phase of PCT Application No. PCT/US2006/001130, filed Jan. 12, 2006, which claims the benefit of U.S. Provisional Application No. 60/643,535, filed Jan. 12, 2005.

STATEMENT REGARDING FEDERALLY SPONSORED RESEARCH OR DEVELOPMENT

This invention was made with government support under Grant No. R21 EB002857 awarded by The National Institutes of Health. The government has certain rights in the invention.

BACKGROUND OF THE INVENTION (1) Field of the Invention

The present invention generally relates to vectors for gene delivery to mammalian cells. More specifically, the invention is directed to the use of nonpathogenic mycobacteria as vectors to deliver genes to mammalian cells that can be expressed by the mammalian cells.

(2) Description of the Related Art

REFERENCES

Bright, R. A., Ross, T. M., Subbarao, K., Robinson, H. L., and Katz, J. M. (2003). Impact of glycosylation on the immunogenicity of a DNA-based influenza H5 HA vaccine. Virology 308(2), 270-8.

CDC (2003). Update: Influenza activity—United States, Dec. 7-13, 2003. MMWR Morb Mortal Wkly Rep 52(50), 1232-1234.

Demicheli, V., Rivetti, D., Deeks, J. J., and Jefferson, T. O. (2000). Vaccines for preventing influenza in healthy adults. Cochrane Database Syst Rev(2), CD001269. Harper et al., 2003

Fennelly, G. J., Khan, S. A., Abadi, M. A., Wild, T. F., and Bloom, B. R. (1999). Mucosal DNA vaccine immunization against measles with a highly attenuated Shigella flexneri vector. J Immunol 162(3), 1603-10.

Flint J L, Kowalski J C, Karnati P K, Derbyshire K M. The RD1 virulence locus of Mycobacterium tuberculosis regulates DNA transfer in Mycobacterium smegmatis. Proc Natl Acad Sci U S A. 2004 Aug. 24; 101(34):12598-603.

Garcia-del Portillo F, Finlay B B. The varied lifestyles of intracellular pathogens within eukaryotic vacuolar compartments. Trends Microbiol. 1995 October; 3(10):373-80.

Gorse, G. J., Campbell, M. J., Otto, E. E., Powers, D. C., Chambers, G. W., and Newman, F. K. (1995). Increased anti-influenza A virus cytotoxic T cell activity following vaccination of the chronically ill elderly with live attenuated or inactivated influenza virus vaccine. J Infect Dis 172(1), 1-10.

Grillot-Courvalin C, Goussard S, Courvalin P. Wild-type intracellular bacteria deliver DNA into mammalian cells. Cell Microbiol. 2002 March; 4(3): 177-86.

Haeseleer F, Pollet J F, Haumont M, Bollen A, Jacobs P. Stable integration and expression of the Plasmodium falciparum circumsporozoite protein coding sequence in mycobacteria. Mol Biochem Parasitol. 1993 January; 57(1):117-26.

Lee, P. Y., Matchar, D. B., Clements, D. A., Huber, J., Hamilton, J. D., and Peterson, E. D. (2002). Economic analysis of influenza vaccination and antiviral treatment for healthy working adults. Ann Intern Med 137(4), 225-31.

Poland, G. A., Rottinghaus, S. T., and Jacobson, R. M. (2001). Influenza vaccines: a review and rationale for use in developed and underdeveloped countries. Vaccine 19, 2216-20.

Potter, C. W., and Oxford, J. S. (1979). Determinants of immunity to influenza infection in man. Br Med Bull 35(1), 69-75.

Sizemore, D. R., Branstrom, A. A., and Sadoff, J. C. (1995). Attenuated Shigella as a DNA delivery vehicle for DNA-mediated immunization. Science 270(5234), 299-302.

Thompson, W. W., Shay, D. K., Weintraub, E., Brammer, L., Cox, N., Anderson, L. J., and Fukuda, K. (2003). Mortality associated with influenza and respiratory syncytial virus in the United States. *JAMA* 289(2), 179-86.

Yoshikawa, T., Suzuki, Y., Nomoto, A., Sata, T., Kurata, T., and Tainura, S. (2002). Antibody responses and protection against influenza virus infection in different congenic strains of mice immunized intranasally with adjuvant-combined A/Beijing/262/95 (H1N1) virus hemagglutinin or neuraminidase. *Vaccine* 21(1-2), 60-6.

Babiuk et al., Poult. Sci., 82(6): 870-5, 2003.

Behr et al., Science, 284: 1520-3, 1999.

Bot et al., Int. Immunol. 9: 1641-50, 1997.

Bot et al., 5(3): 197-210, 1998.

Davis et al., 4(6): 733-40, 1993.

Eo et al., J. Immunol. 166: 5473-9, 2001.

Freund et al., Arch, Pathol. 50: 108-121, 1950.

Freund and Stone, J. Immunol. 82: 560-567, 1959.

Haley, et al., Immunology 96: 114-121, 1999.

Hsu et al., Proc. Natl. Acad. Sci. U S A 100(21): 12420-5, 2003.

Johnson, et al., J. Gen. Virol. 82: 1737-45, 2000.

Mahairas et al, J. Bacteriol. 178: 1274-82, 1996.

Molife and Hancock, Crit. Rev. Oncol. Hematol. 44: 81-102, 2002.

Pavelka, et al., J. Bacteriol. 178: 6496-6507, 1996.

Pavelka, et al., J. Bacteriol., 181: 4780-4789, 1999.

Powell et al., U.S. Pat. No. 6,682,729.

Shepel and Klugerman, J. Bacteriol. 85: 1150-1155, 1963.

Snapper, et al., Mol. Microbiol. 4: 1911-1919, 1990.

Stover, et al., Nature 351: 456-460, 1991.

Soloranzo, et al., J. Gen. Virol. 81: 737-42, 2000.

Spencer et al., J. Infect. Dis. 136: 171-5, 1977.

Stanley et al., Proc. Natl. Acad. Sci. U S A 100(22): 13001-6, 2003.

Thole et al., Infect. Immun. 55 1466-75, 1987.

Thomsen et al., Proc. Natl. Acad. Sci. U S A 81: 659-663, 1984.

Ulmer et al., Science 259: 1745-1749, 1993.

Vecino, et al., Virology, 325: 192-9, 2004.

Vilcheze, et al., J. Bacteriol. 182(14): 4059-67, 2000.

Wolff et al., Science 247: 1465-1468, 1990.

The discovery that the direct intramuscular injection of plasmid DNA encoding protective antigens into mice was sufficient to induce protective immunity (Wolff et al. 1990; Ulmer et al. 1993) created great excitement and hopes that similar immunizations and "gene therapy" could be used in humans. Unfortunately, although DNA vaccination elicits both humoral and cytotoxic immunity, in humans and livestock the immune responses are usually weak and short-lived (Babiuk et al. 2003). In an attempt to improve the efficiency of DNA immunization, bacteria have recently been studied as gene delivery vectors. Through a process called 'bactofection' (Powell et al., 1999), intracellular bacteria enter a mammalian cell and release a DNA plasmid for uptake into the nucleus. As the bacterial carrier replicates the plasmid and directly transports it inside a host cell, the same level of immunization can be achieved with fewer DNA molecules than a naked DNA vaccine, also eliminating the need for large-scale plasmid production and purification. As the encoded gene products are expressed by the vaccinated host, antigens can be programmed to present on either or both MHC classes to optimize both antigen-specific CD4+ and CD8+ T cell responses, and can be secreted while maintaining the proper folding and glycosylation for antibody recognition.

The bacterial vector may also act as a natural adjuvant to enhance the immune response of the original DNA vaccine. The bacteria tested for gene delivery thus far include *Shigella flexneri*, *Listeria monocytogenes*, *Salmonella typhimurium* and invasive *Escherichia coli*, which are all attenuated intracellular pathogens that naturally target the digestive tract (Grillot-Courvalin et al. 2002). This offers the additional benefit of direct mucosal immunization and targeting the vaccine to immune cells that have evolved to respond to these infections. Oral or intranasal vaccination also eliminates the need for needle injection, making the process simpler, less expensive and more acceptable to the public.

It would be desirable to have additional bacteria, including those that are already US FDA approved, and widely used in humans (for example, *Mycobacteria bovis*, BCG used in bladder cancer immunotherapy in the US, and, internationally, as a vaccine against tuberculosis) that are capable of transferring expressible genes to mammalian cells. In particular, endosome-residing bacteria that can transfer genes to mammalian cells would be desirable. The present invention addresses that need.

SUMMARY OF THE INVENTION

The inventors have discovered that *Mycobacterium smegmatis* is capable of transferring DNA to its host mammalian cell, allowing the DNA to be expressed under the control of the mammalian control elements (e.g., promoters).

Thus, the present invention is directed to mycobacteria comprising a recombinant gene operably liked to a mammalian promoter that directs expression of the recombinant gene from a mammalian cell.

The invention is also directed to mammalian cells comprising any of the above mycobacteria.

Additionally, the invention is directed to mycobacterial plasmids capable of replication in a mycobacterium. The plasmids comprise a recombinant gene operably liked to a mammalian promoter that directs expression of the recombinant gene from a mammalian cell.

The invention is further directed to methods of expressing a recombinant gene in a mammalian cell. The methods comprise infecting the cell with any of the above-described mycobacteria.

DETAILED DESCRIPTION OF THE INVENTION

Figure 1:
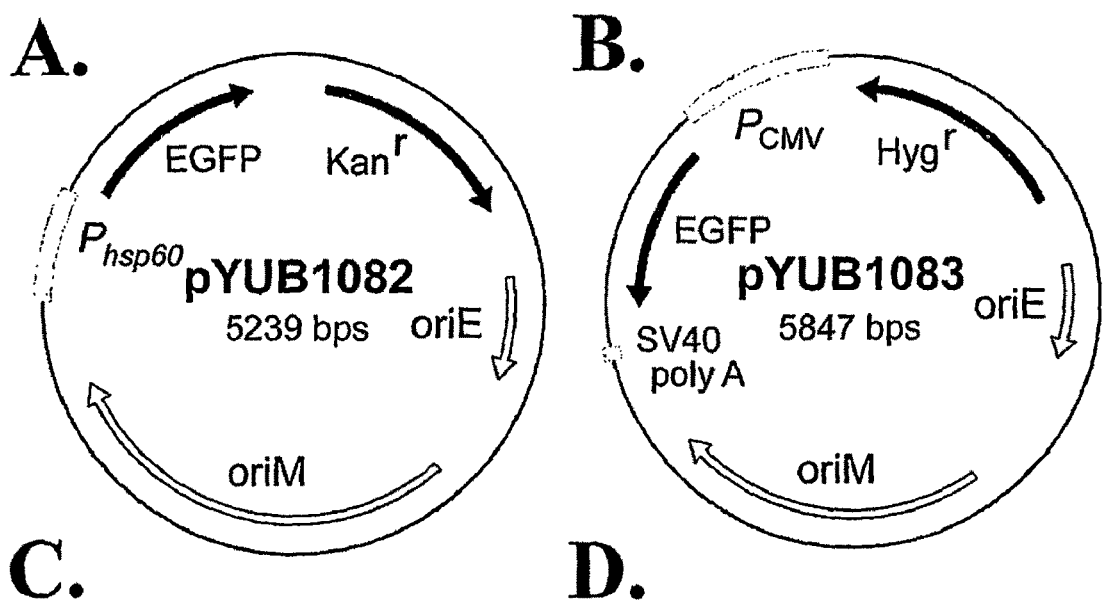
FIG. 1 is diagrams and graphs showing enhanced green fluorescent protein (EGFP) expression vectors and their expression by *M. smegmatis*. Mycobacterial shuttle plasmids were constructed for GFP expression under the mycobacterial hsp60 promoter (Panel A) or the eukaryotic immediate-early CMV promoter/enhancer (Panel B). Abbreviations: oriE, origin of replication in *E. coli*.; oriM, origin of replication in mycobacteria; Kan$^r$, kanamycin resistance gene Hyg$^r$, hygromycin resistance gene. Mycobacterial transformants with the pYUB1082 plasmid (mc$^2$4556) or pYUB1083 plasmid (mc$^2$4557) were cultured and analyzed by flow cytometry for GFP expression (C and D).
Figure 1:
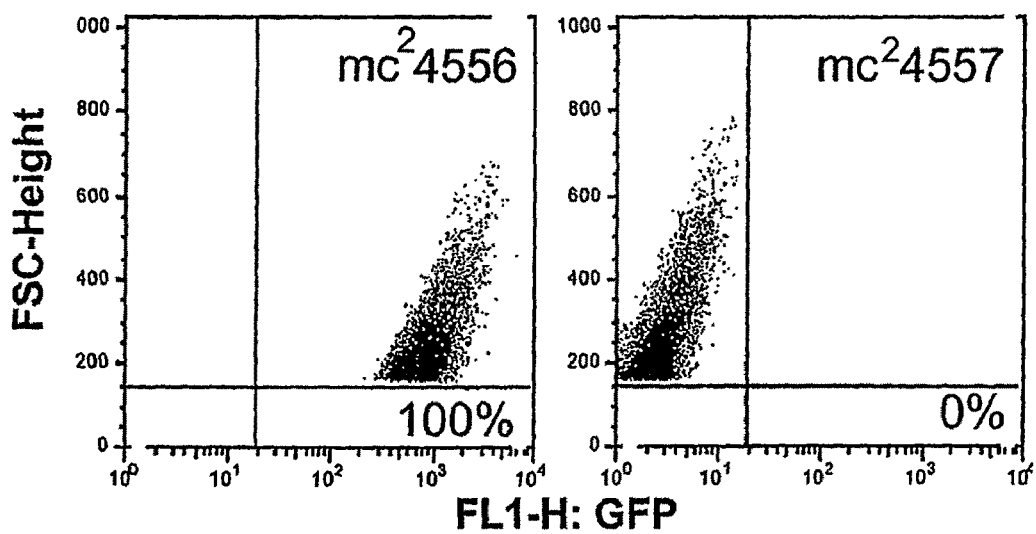

The inventors have discovered that mycobacteria are capable of transferring DNA to its host mammalian cell, allowing the DNA to be expressed under the control of mammalian promoters. See Examples below. This discovery newly allows the use of a mycobacterium as a vector to deliver DNA to a mammalian cell such that the DNA can be transcribed by the mammalian cell. This would permit genetic immunization or delivery of therapeutic genes (e.g. to bladder cancer cells after intravesicular instillation of recombinant mycobacteria).

Thus, the present invention is directed to mycobacteria comprising a recombinant gene operably liked to a mammalian promoter that directs expression of the recombinant gene from a mammalian cell. The mycobacteria can be of any species, including *M. smegmatis*, *M. bovis* BCG, *M. avium*, *M. vaccae*, *M. phlei*, *M. fortuitum*, *M. lufu*, *M. paratuberculosis*, *M. habana*, *M. scrofulaceum*, *M. intracellulare*, *M. tuberculosis*, or *M. kansasii*. Preferably, the mycobacterium is an attenuated strain of a pathogenic mycobacterium. More preferably, the mycobacterium nonpathogenic (i.e., does not normally cause disease. Examples of nonpathogenic mycobacteria are *M. smegmatis*, *M. phlei*, *M. lufu*, *M. habana* or *M. vaccae*. Most preferably, the mycobacterium is *M. smegmatis* or *M. bovis* BCG.

The inventors have also found that a mycobacterium is more effective in transferring the recombinant gene to the host mammalian cell if that mycobacterium is more effective at conjugation. See Example 1. Thus, it is preferred if the mycobacterium is effective at conjugation. Most preferably, the mycobacterium is capable of hyperconjugation. As used herein, "hyperconjugation" is the ability of a mutant mycobacterium to conjugate with increased frequency from the wild-type mycobacterium. See, e.g., Flint et al., 2004. Where the mycobacterium is *Mycobacterium smegmatis*, the preferred strain is mc$^2$155 or a derivative thereof. See Example 1.

These methods are not limited to the use of any particular mammalian promoter, provided the promoter is capable of directing expression of the recombinant gene in the host cell. The skilled artisan could identify without undue experimentation a suitable promoter for any particular application and mammalian cell type. In some preferred embodiments, the promoter is a human cytomegalovirus immediate-early promoter (CMVp). See Example 1.

Other control elements useful in mammalian cells can also be utilized in the present invention. Examples include enhancers and polyadenylation signals. See Example 1, where the CMV enhancer and bovine growth hormone polyadenylation signal was utilized.

The present invention is not narrowly limited to the use of any particular recombinant gene. It is envisioned that the present invention can be used to express any gene under the control of the mammalian cell. Non-limiting examples of useful genes include a protein, such as a cytokine, an essential protein (e.g., enzyme) that is not expressed by the mammalian cell (e.g., Factor IX for hemophilia patients), a cytokine (e.g., growth hormone), an antigen of a neoplasm, tumor or cancer, or an antigen of a pathogen, in order to induce immunity in a mammal harboring the mammalian cell. Examples of pathogens (e.g., human pathogens) where antigens useful in the present method can be utilized include viruses (e.g., HIV, hepatitis C virus, herpes virus, influenza, smallpox, diphtheria, tetanus, measles, mumps, rabies, poliovirus etc), bacteria (e.g., pathogenic mycobacteria, *Salmonella* sp., etc.), and eukaryotic parasites (e.g., malaria, *Leishmania*, etc.).

The gene to be expressed in the mammalian cell can be present on any type of intracellular mycobacterial vector. In preferred embodiments, the gene is on a mycobacterial plasmid. As established in the Example, a useful mycobacterial plasmid for these purposes is a pAL500-based plasmid.

As shown in Example 2 below, higher plasmid copy numbers is achieved if a replication protein such as RepA and/or RepB is overexpressed. Thus, it is preferred if the mycobacterium overexpresses a replication protein derived from the plasmid. More preferably, the plasmid is pAL500-based and the replication protein is RepA or RepB. The mycobacterium can also overexpress both RepA and RepB.

A preferred mycobacterium of the invention is an *Mycobacterium smegmatis* comprising a recombinant gene operably liked to a mammalian promoter that directs expression of the recombinant gene from a mammalian cell, where
(a) the *Mycobacterium smegmatis* is capable of hyperconjugation and is of strain Mc$^2$155 or a derivative thereof;
(b) the recombinant gene is on a mycobacterial plasmid;
(c) the mycobacterial plasmid is a pAL500-based plasmid;
(d) the promoter is a human cytomegalovirus immediate-early promoter; and
(e) the *Mycobacterium smegmatis* overexpresses a RepA and/or RepB protein derived from a pAL500-based plasmid.

The invention is also directed to mammalian cells comprising any of the above mycobacteria.

Preferably, the mammalian cells in these embodiments are human cells, although the invention method would be expected to work in cells of any mammal. In more preferred embodiments, the human cell is part of a living human.

The mammalian cell is not limited to any particular type of cell. See Example 1, where successful gene transfer was achieved into macrophages, fresh human peripheral blood monocytes, and murine MB49 bladder tumor cells. It is thus believed that the present invention would work in any mammalian cell that is capable of being infected with *M. smegmatis*.

Additionally, the invention is directed to mycobacterial plasmids capable of replication in a mycobacterium. The plasmids comprise a recombinant gene operably liked to a mammalian promoter that directs expression of the recombinant gene from a mammalian cell. Preferably, the mycobacterial plasmid is a pAL500-based plasmid. It is also preferred that the promoter is a human cytomegalovirus immediate-early promoter. Additionally, a gene encoding an alpha virus replicase can be useful on these invention plasmids.

The invention is further directed to methods of expressing a recombinant gene in a mammalian cell. The methods comprise infecting the cell with any of the above-described mycobacteria. Preferably, the mammalian cell is a human cell. The mammalian cell can be part of a living mammal, for example, a recipient of a vaccine comprising the mycobacteria. Alternatively, the mammalian cell can be infected in vitro, then optionally transplanted into a mammalian recipient (ex vivo).

Preferably, the mammalian cell is a macrophage, dendritic cell or tumor cell; most preferably, the mammalian cell is a macrophage.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

Characterization of Mycobacterial Bactofection to Eukaryotic Cells and Mice

Example Summary

Recently, much attention has been given to the use of bacteria as vectors for gene transfer into mammalian cells. This system is being explored as a means of DNA vaccination, as naked DNA vaccines are largely unsuccessful in humans. Characterized herein is the plasmid transfer ability of mycobacteria, an immunogenic bacterial species that targets and persists inside phagocytic monocytes, making it an attractive candidate for vaccine delivery. Using fluorescent protein expression as a means of visualizing and quantitating the efficiency of DNA transfer, we transformed the fast-growing *Mycobacterium smegmatis* with plasmids carrying the reporter genes under the control of either mycobacterial or eukaryotic promoters. Upon infection of both phagocytic and non-phagocytic cells lines, expression by the bacteria and the host cell was identified via microscopy and flow cytometry, and gene transfer was correlated with different levels of infection. There was an increased level of plasmid transfer to eukaryotic cells infected with hyperconjugating *M. smegmatis* mutants, however, mutants displaying a decreased conjugation phenotype were still capable of transfecting cells, suggesting that other mechanisms allow DNA release into the host cell. When these mutants were transformed with eukaryotic expression plasmids encoding Influenza hemagglutinin, they also conferred partial protection to mice from lethal challenge with the virus.

Introduction

This study presents mycobacteria as a new candidate for DNA vaccine delivery. In contrast to the other bacterial species currently being tested, *Mycobacteroum bovis* BCG and *Mycobacterium smegmatis* are nonpathogenic, yet retain powerful immunomodulating properties, as shown by their use in adjuvants (Freund et al. 1950; Freund and Stone 1959; Shepel and Klugerman 1963) and cancer therapy (Haley, et al. 1999; Molife and Hancock 2002). BCG is especially attractive as it is accepted as safe for infants and can be given orally, and it is currently the most widely administered vaccine in the world.

To examine whether mycobacteria are capable of bactofection, experiments were done in vitro using plasmids encoding green fluorescent protein (GFP) or dsRed fused to mycobacterial or eukaryotic promoters, to visualize and contrast expression by the bacteria and the infected mammalian cells.

Fluorescence was observed throughout the cytoplasm of both a phagocytic macrophage cells (RAW) and nonphagocytic carcinoma cells (HeLa) infected with mycobacteria delivering the eukaryotic GFP-expression plasmid, demonstrating successful DNA transfer from the bacteria to the host cell. In contrast, cells infected with bacteria bearing plasmids with GFP or dsRed under a mycobacterial promoter showed only scattered punctuated fluorescence, representing expression by the bacteria.

Successful bacterial uptake did not always result in GFP expression by the host cells, implying that factors specific to the cells or to the infecting bacteria determine the efficiency of gene delivery. The mechanism by which DNA escapes the bacterium and enters the eukaryotic cell nucleus remains a mystery for all bacterial species that have been studied to date, although the ability of *S. flexneri* and *L. monocytogenes* to escape the phagolysosome is considered to be important for their ability to mediate plasmid transfer (Sizemore et al. 1995; Grillot-Courvalin et al. 2002). In addition, auxotrophic mutants or species expressing lysins that induce bacterial death once internalized by the cell have demonstrated improved levels of bactofection (Daiji et al. 1997; Dietrich et al. 1998). The ability of auxotrophic mutants of BCG and *M. smegmatis* to deliver eukaryotic GFP expression plasmids to mammalian cells was tested, but no significant difference was measured between the mutants and wild-type strains.

The conjugation system, which mediates DNA transfer to other bacteria, was then tested for its effect on plasmid transfer from *Mycobacteria* to host cells. The recent discovery of *M. smegmatis* transposon insertion mutants with a "hyperconjugation" phentotype (Flint et al. 2004), led us to question whether these mutants might also be more efficient at bactofection. It was found that one mutant in particular, mKD211, mediated a slight but significant increase in DNA transfer over the wildtype strain, which disappeared upon complementation. Interestingly, a mutant displaying severely reduced conjugation compared to wildtype was still capable of mediating plasmid transfer to mammalian cells. It therefore appears that these conjugation mutations have only an indirect effect on bactofection ability, and that multiple pathways for DNA release exist in *Mycobacteria*.

To test whether *Mycobacteria* could also deliver DNA plasmids in vivo, *M. bovis* BCG and *M. smegmatis* strains were transformed with the pYUB2406 hemagglutinin-encoding plasmid previously used in an influenza protection study using *S. flexneri* (Vecino et al. 2004). There, mice immunized with mycobacteria carrying the pYUB2406 plasmid showed improved survival after viral challenge over those immunized with strains carrying an empty vector. The difference was especially significant in mice immunized with a hyperconjugating mutant, although the level of overall protection was less than observed with *S. flexneri*. Anti-Influenza specific IFN-γ secreting T cells were only present in mice immunized with *Mycobacteria* bearing pYUB2406, although no anti-Influenza serum antibody could be detected.

Materials and Methods

Plasmid purification and construction. Table 1B lists the plasmids used in this work. The egfp gene was cloned out of pEGFP-N1 (Clontech, Mountain View, Calif.) as an EcoR1 fragment and ligated into pMV261 digested with EcoR1 to create pYUB1082. The $P_{CMV}$-egfp-sv40 polyA region was also cloned out of pEGFP-N1 as an AseI-XbaI digested fragment and ligated into pMV206 linearized with XbaI to create pYUB1083. The $P_{msp12}$::dsRed2 region of pYUB1086 (a generous gift from L. Ramakrishnan) was PCR amplified with primers 5' AAAAAAACGCGTGCCATCCGTGGC 3' (SEQ ID NO: 1) and 5' GCTGTTACGCGTGTAAGCAGA-CAG 3' (SEQ ID NO: 2) and digested with MluI. The product was ligated into pYUB1083 that had been cleaved with MluI to create pYUB1085.

All plasmids were purified from *Escherichia coli* DH5α transformants using Qiagen miniprep or midiprep columns as indicated by the manufacturer (Qiagen, Valencia, Calif.).

Mycobacterial strains and culture conditions. Table 1A lists the mycobacterial strains used in this work. *Mycobacteria* were grown in Middlebrook 7H9 broth (Becton Dickinson, Franklin Lakes, N.J.) with 0.05% Tween 80 at 37° C., supplemented with 40 mg/ml lysine, 0.1 mg/ml of diaminopimilic acid, or 48 mg/ml of pantothenate according to the auxotroph (Sigma Chemical Co., St. Louis, Mo.). Plasmids were electroporated into mycobacteria as previously described (Snapper et al. 1990; Wards and Collins 1996). Selective conditions were subsequently used to screen and maintain transformants (20 μg/ml kanamycin, 50 μg/ml of hygromycin, 20 μg/ml of apramycin) (Sigma). Cultures were started from individual colonies grown on Middlebrook 7H10 plates with the appropriate antibiotic and supplements, or subcultured from frozen stocks of previously screened clones. Samples were grown to late-log phase ($OD_{600}$=1) and either administered directly to eukaryotic cell cultures or diluted in PBS-Tween for direct injection into mice. Temperature sensitive strains were grown at 42° C. for four hours prior to mouse immunizations to begin stimulate lysis (Vilcheze et al., 2000). Cell counts were verified by plating serial dilutions of the inoculums.

TABLE 1

| | Relevant characteristics | Source or reference |
|---|---|---|
| A. Mycobacterial and viral strains. | | |
| Strain | | |
| *M. smegmatis* mc²155 | efficient plasmid transformation (ept-l) | Snapper et al, 1990 |
| *M. smegmatis* mc²1278 | ask1::aph, DAP auxotroph, Km$^R$ | Pavelka et al., 1996 |
| *M. smegmatis* mc²2359 | attB::pYUB412::ndh inhA40, Inh$^R$, TS | Vilcheze et al., 2000 |
| *M. smegmatis* mc²4519 | ☐esat6-cfp10 | [2] |
| *M. smegmatis* mc²4553 | mc²155 w/pMV261, Km$^R$ | Stover et al., 1991 |
| *M. smegmatis* mc²4554 | mc²155 w/pYUB1060, Hy$^R$ | Stover et al., 1991 |
| *M. smegmatis* mc²4556 | mc²155 w/pYUB1082, Km$^R$ | [4] |
| *M. smegmatis* mc²4557 | mc²155 w/pYUB1083, Hy$^R$ | This work |
| *M. smegmatis* mc²4558 | mc²155 w/pYUB1084, Ap$^R$ | This work |
| *M. smegmatis* mc²4559 | mc²155 w/pYUB1085, Hy$^R$ | This work |
| *M. smegmatis* mc²4560 | mc²155 w/pYUB1086, Km$^R$ | [5] |
| *M. smegmatis* mc²4562 | transposon mutant in Rv3868 homologue, Km$^R$ | Flint et al., 2004 |
| *M. smegmatis* mKD211 | transposon mutant in Ms_orf, Km$^R$ | Flint et al., 2004 |
| *M. smegmatis* mc²4565 | mKD211 complemented with m. TB RD1, Km$^R$, Hy$^R$ | Flint et al., 2004 |

TABLE 1-continued

| | Relevant characteristics | Source or reference |
|---|---|---|
| M. smegmatis mc²4566 | transposon mutant in Ms4898, Km$^R$ | [1] |
| M. smegmatis mc²4568 | mc²4562 w/pYUB1083, Km$^R$, Hy$^R$ | This work |
| M. smegmatis mc²4571 | mKD211 w/pYUB1083, Km$^R$, Hy$^R$ | This work |
| M. smegmatis mc²4572 | mc²4565 w/pYUB1084, Km$^R$, HyR, Ap$^R$ | This work |
| M. smegmatis mc²4573 | mKD211 w/pYUB1085, Km$^R$, Hy$^R$ | This work |
| M. smegmatis mc²4574 | mc²4566 w/pYUB1083, Km$^R$, Hy$^R$ | [1] |
| M. smegmatis mc²4575 | mc²1278 w/pYUB1083, DAP auxotroph, Km$^R$, Hy$^R$ | This work |
| M. smegmatis mc²4576 | mc²4519 w/pYUB1083, Hy$^R$ | This work |
| M. smegmatis mc²4577 | mc²2359 w/pMV261, Inh$^R$, TS, Km$^R$ | This work |
| M. smegmatis mc²4579 | mc²2359 w/pYUB2406, Inh$^R$, TS, Km$^R$ | This work |
| M. smegmatis mc²4597 | mc²155 w/pYUB2406, Km$^R$ | This work |
| M. smegmatis mc²4598 | mc²4562 w/pYUB1060, Km$^R$, Hy$^R$ | This work |
| M. smegmatis mc²4599 | mc²4562 w/pYUB1090, Km$^R$, Hy$^R$ | This work |
| M. smegmatis mc²4600 | mKD211 w/pYUB1060, Km$^R$, Hy$^R$ | This work |
| M. smegmatis mc²4601 | mKD211 w/pYUB1090, Km$^R$, Hy$^R$ | This work |
| M. bovis BCG Pasteur | vaccine strain | |
| M. bovis BCG mc²1604 | ☐lysA, lysine auxotroph | Pavelka et al., 1999 |
| M. bovis BCG mc²4580 | Pasteur BCG w/pMV261, Km$^R$ | This work |
| M. bovis BCG mc²4581 | Pasteur BCG w/pYUB1082, Km$^R$ | This work |
| M. bovis BCG mc²4582 | Pasteur BCG w/pYUB1083, Hy$^R$ | This work |
| M. bovis BCG mc²4583 | Pasteur BCG w/pYUB2406, Km$^R$ | This work |
| M. bovis BCG mc²4584 | mc²1604 w/pMV261, lysine auxotroph, Km$^R$ | This work |
| M. bovis BCG mc²4585 | mc²1604 w/pYUB1083, lysine auxotroph, Hy$^R$ | This work |
| M. bovis BCG mc²4587 | mc²1604 w/pYUB2406, lysine auxotroph, Km$^R$ | This work |
| M. bovis BCG mc²4588 | mc²6000 w/pMV261, pantothenate auxotroph, Hy$^R$, Km$^R$ | This work |
| M. bovis BCG mc²4589 | mc²6000 w/pYUB1087, pan. auxotroph, Hy$^R$, Km$^R$ | This work |
| M. bovis BCG mc²4602 | mc²6000 w/pYUB2406, pan. auxotroph, Hy$^R$, Km$^R$ | This work |
| M. bovis BCG mc²6000 | ☐panCD, pantothenate auxotroph, Hy$^R$ | [3] |
| Influenza A/WSN/33 | mouse adapted strain | |
| Influenza D2A/WSN/33 | neuraminidase mutant; attenuated | Soloranzo et al, 2000 |

B. Plasmids

| Plasmid | | |
|---|---|---|
| pMV206 | shuttle vector, Km$^R$ | Stover et al., 1991 |
| pMV261 | shuttle vector, Km$^R$ | Stover et al., 1991 |
| pYUB1058 | pMV206, Hy$^R$ | Stover et al., 1991 |
| pYUB1060 | pMV261, Hy$^R$ | Stover et al., 1991 |
| pYUB1063 | pMV206, Ap$^R$ | This work |
| pYUB1082 | pMV261 with P$_{hsp6}$::egfp, Km$^R$ | [4] |
| pYUB1083 | pYUB1058 with P$_{CMV}$::egfp, Hy$^R$ | [6] |
| pYUB1084 | pYUB1063 with P$_{CMV}$::egfp, Ap$^R$ | This work |
| pYUB1085 | pYUB1083 with P$_{msp12}$::dsRed2 P$_{CMV}$::egfp, Hy$^R$ | This work |
| pYUB1086 | pMV261 with Pmsp12::dsRed2, Km$^R$ | [5] |
| pYUB1087 | pMV261 with P$_{CMV}$::egfp, Km$^R$ | This work |
| pYUB1088 | pMV206 with P$_{CMV}$::egfp, Km$^R$ | [6] |
| pYUB1090 | pYUB2406, Hy$^R$ | Vecino et al., 2004 |
| pYUB2406 | pMV261 with P$_{CMV}$::HA, Km$^R$ | Vecino et al., 2004 | abbreviations: Km = kanamycin, Hy = hygromycin, Ap = apramycin
[1] laboratory of K. Derbyshire: unpublished
[2] K. Lawrence; laboratory of W R. Jacobs Jr., unpublished
[3] V. Sambandamurthy; laboratory of W R. Jacobs Jr., unpublished
[4] T. Hsu; laboratory of W R. Jacobs Jr., unpublished
[5] laboratory of L. Ramakrishnan; unpublished
[6] W. Vecino; laboratory of W R. Jacobs Jr., unpublished Influenza virus preparation and administration. Mouse-adapted Influenza A/WSN/33 (H1N1) was grown in the allantoic cavity of embryonated chicken eggs. $10^4$ pfu of virus was injected into ten day-old eggs with a 28½ gauge needle and incubated at 37° C. for two days. Embryos were sacrificed by incubating eggs at 4° C. for four hours, and allantoic fluid was pipetted from the eggs and pooled. Madin Darby kidney carcinoma (MBCK) cells were grown to confluency in REM medium (Biowhittaker, Cambrex, East Rutherford, N.J.) with 10% heat-inactivated Fetal Bovine Serum (FBS) (Gibco, invitrogen, Grand Island, N.Y.) and infected with serial dilutions of virus samples for 1 hour at room temperature. Cells were overlayed with agar and incubated 2-3 days at 37° C. for plaque titration. Samples were aliquoted and frozen at −70° C. until ready for use. The attenuated Influenza D2A/WSN/33 strain (Solorzano et al. 2000) was amplified and isolated from cultures of MBCK cells, then titrated and prepared as described above.

Mammalian cell culture conditions infections and staining. RAW (murine macrophage cell) and HeLa (human cervix adenocarcinoma) lines were grown in Dulbecco's modified Eagle's Medium (DMEM) supplemented with 10% FBS, 2% HEPES buffer and 5% NCTC-109 medium (Gibco). Cells were transferred at a concentration of $1-2\times10^5$ cells/well in a 48-well plate and incubated at 37° C., 10% $CO_2$ for 2-24 hours before infection to generate semi-confluent lawns of cells. Freshly grown mycobacteria were added to the cells at an MOI of 1, 3, 10, 50 or 100 to a total volume of no more than 350 μl/well in a 48-well plate. Lipofectamine (Invitrogen) was diluted 1:50 in Opti-Mem medium (Gibco) and incubated at room temperature (RT) for 5 minutes before being added to 10 μg of DNA per sample in an equal volume of medium. Samples were incubated 20 minutes at RT before being added to cells. After a 3-5 hour incubation, cells were washed three times with DMEM. Cells were then incubated in 500 μl or 2 ml of medium with 50 μg/ml of gentamycin (Gibco) to kill extracellular bacteria. After 1-5 days, cells were observed under the microscope for fluorescence. For nuclear visualization, some cells were stained with Vybrant violet DNA dye (Molecular Probes, Invitrogen, Eugene, Oreg.). 1 μl of dye was added directly to cells in a 48-well culture plate, with an average of 5×10$^5$ cells/well covered in 500 μl of media, and incubated at 37° C. in the dark for 30 minutes prior to imaging. At the appropriate time point, all cells were trypsinized and resuspended in 4% FBS/PBS. Samples were stored at 4° C. until ready for FACS analysis.

Microscopic imaging and FACS analysis. Live cell samples were observed using an Olympus IX 81 microscope (Melville, N.Y.) with a Cooke Sensicam QE air-cooled CCD camera and a mercury lamp for fluorescence illumination. Images were collected using IPLab Spectrum software (Scanlytics, Rockville, Md.) at 10× or 40× magnification. Adobe Photoshop (Adobe Systems, San Diego, Calif.) was used to restore color and merge images captured using different fluorescence filters or normal light (phase contrast) illumination. Fluorescence of a minimum of 10$^5$ cells per sample was measured by flow cytometry using a FACScan or FACS Calibur cytometer and CellQuest software (Becton Dickinson). Data was further analyzed with the FloJo software (Tree Star, Inc., Ashland, Oreg.).

Animals and immunization. Groups of four-to-six week-old mice female BALB/c mice (Charles River, Wilmington, Mass.) were immunized two or four times at 3-4 week intervals. Intranasally administered samples were prepared in a total volume of 35-50 μl, which was slowly pipetted into the nares of anesthetized mice while they lay supine. A positive control group of mice was injected with 50 μl of purified pYUB2406 DNA diluted in sterile saline to a concentration of 1 μg/μl into the anterior tibialis muscle of both legs, five days after receiving an injection of cardiotoxin (Latoxan, Rosans, France) as previously described (Davis et al. 1993). Samples were administered at a dose of 10$^6$ CFU of BCG or *M. smegmatis*. Negative control groups were injected with PBS or strains carrying empty plasmids lacking the HA gene. Attenuated Influenza strain D2A/WSN/33 was injected intranasally at 10$^4$ pfu in some mice. Animals were anesthetized with isofluorane or avertin prior to immunization and phlebotomy. The mouse study protocol was approved by the AECOM Animal Institute Committee and Institute for Animal Studies.

ELISPOT assay. The frequency of Influenza virus-specific IFN-γ producing cells from splenocytes of immunized mice was quantitated using a live Influenza virus-based ELISPOT assay as previously described (Vecino et al. 2004). Briefly, pooled splenocytes from 5 mice in each immunization group were resuspended in supplemented RPMI 1640 media (Gibco) and 10% heat-inactivated FBS and cultured with an equal number of irradiated stimulator cells from naïve Balb/c mice. Ninety-six well nitrocellulose-bottomed microtiter plates (Millipore, Bedford, Mass.) were pre-coated overnight with murine IFNγ-specific monoclonal antibody (mAb R46, Pharmingen, San Diego, Calif.) at a concentration of 10 μg/ml. Plates were washed three times in PBS and blocked with RPMI 10% FBS for two hours. Cells were added in triplicate from 1-5×10$^5$ cells per well and incubated for 24 hours. After washes, biotinylated anti-mouse IFN☐ antibody (clone XMG 1.2, BD Pharmingen) diluted 1:500 in PBST/5% FBS was added to each well and plates were incubated for 2 hours at RT. Streptavidin-alkaline phosphatase (BD Pharmingen) diluted 1:400 in PBST/5% FBS was added to each well after washes and incubated for an additional 2 hours. Plates were developed using the Sigma Fast BCIP/NBT substrate. Spots were counted using a stereomicroscope with overhead illumination. The results were expressed as the frequency of influenza-specific IFN-γ-secreting spot forming units (sfu) per million splenocytes after subtracting the background rates of spontaneous IFN-γ secretion among splenocytes from control immunized mice inoculated with either pMV261 or PBS.

Influenza virus challenge. One month after the last immunization, BALB/c mice were challenged with 1×10$^5$ pfu of wild-type influenza A/WSN/33 virus. Mice were weighed and observed daily for signs of morbidity, and euthanized if they lost >30% of their pre-challenge body weight or exhibited clinical signs of pilo-erection, hunched posture, reduced mobility and lost >20% of their pre-challenge body weight.

Statistical analysis. The Prism program was used for statistical data analysis (GraphPad Software, San Diego, Calif.). Survival differences between immunization groups were measured by Logrank (Kaplan-Meir) tests. To analyze ELISPOT data and GFP expression, ANOVA for unpaired samples was performed. Values of $P<0.05$ were considered significant.

Results

Delivery of reporter plasmids to a murine macrophage cell line with *Mycobacterium smegmatis*. To determine whether mycobacteria can deliver DNA plasmids to eukaryotic cells, an extrachromosomal mycobacterial plasmid, pYUB1083, was constructed containing the gfp reporter gene fused to the cytomegalovirus immediate-early promoter/enhancer ($P_{CMV}$) (Thomsen et al. 1984) and transformed into *M. smegmatis*. Flow cytometry was used to demonstrate that the gfp gene was not expressed by the $P_{CMV}$ in *M. smegmatis*, in contrast to expression which was readily detected when transcribed from the hsp60 promoter (Thole et al. 1987) in plasmid pYUB1082 (FIG. 1). This observation confirms that there is no cryptic mycobacterial promoter activity driving GFP expression in *M. smegmatis* transformed with the $P_{CMV}$::gfp plasmid, and thus any resulting fluorescence would reflect plasmid transfer to the macrophage.

As macrophages are the target cell in a mycobacterial infection, DNA transfer was first tested in RAW cells, a murine macrophage cell line, by infecting with *M. smegmatis* harboring pYUB1082 or pYUB1083. Fluorescence microscopy revealed a striking distinction between the pattern of expression in the two groups (FIGS. 2A, B). *M. smegmatis* containing the $P_{CMV}$::gfp plasmid expressed GFP, revealing the presence of individual mycobacteria within cellular vacuoles. In contrast, GFP expression was visible throughout the cytoplasm of RAW cells infected with *M. smegmatis* bearing the $P_{CMV}$::gfp plasmid. As pYUB1083 was shown not to express GFP in mycobacteria, any fluorescence observed in cell infections with this strain would have to be a result of gene transfer through the phagosomal membrane and into the cell nucleus, resulting in expression by the cell and not by the invading bacteria.

Figure 2:
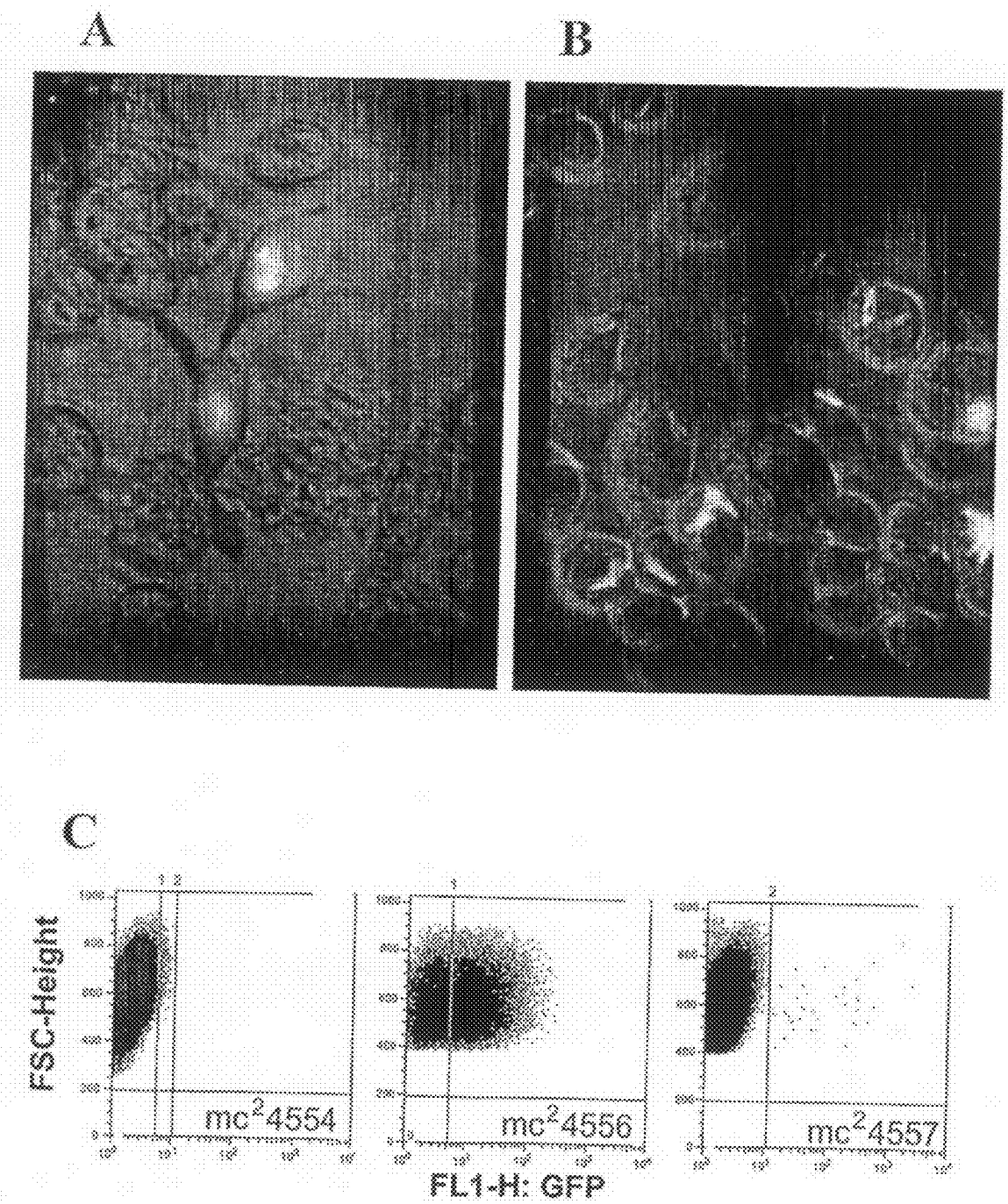
FIG. 2 is florescence micrographs and graphs showing GFP expression by *M. smegmatis* infected RAW cells. RAW cells were infected with mc$^2$4557 (Panel A) or mc$^2$4556 (Panel B) at an MOI of 10 and observed under fluorescence microscopy after 24 hours. Original images taken at 40× magnification. RAW cells infected with mc$^2$4554, mc$^2$4556 or mc$^2$4557 at an MOI of 10 were also collected five days post infection for flow cytometric analysis. Charts representative of a minimum of three experiments are displayed, with quadrant axes aligned to reduce background in high percentage (1) and low percentage (2) GFP-expressing samples (Panel C). The percentage of GFP expression seen in mc$^2$4557 infections can also be adjusted to reflect only the percentage of cells that have internalized bacteria as measured by GFP expression from mc$^2$4556-infected cells at the earliest time point (Day 1 has 96.5±1.65% GFP expression for an MOI of 10. 0.035/0.965=0.0363). RAW cells were infected with mc$^2$4556 at an MOI of 1, 3, 5 or 10, or 10 μg of pYUB1083 DNA with lipofectamine (Lp) and were collected 1 or 5 days post infection and analyzed by flow cytometry (Panel D).

Flow cytometry allows the quantification of eukaryotic cells that either express fluorescent proteins or have internalized fluorescing bacteria. Our observations showed that Day 4 or 5 post-infection was the optimal time point for measuring GFP expression by infected RAW cells (data not shown), at which a mean of 0.035±0.009 percent of the RAW cell population expressed GFP (FIG. 2C). As this percentage is small, careful adjustments were made when subtracting the background fluorescence from negative samples to ensure that the measurements were accurate, and data was collected from triplicate samples in a minimum of three separate experiments.

Figure 2D:
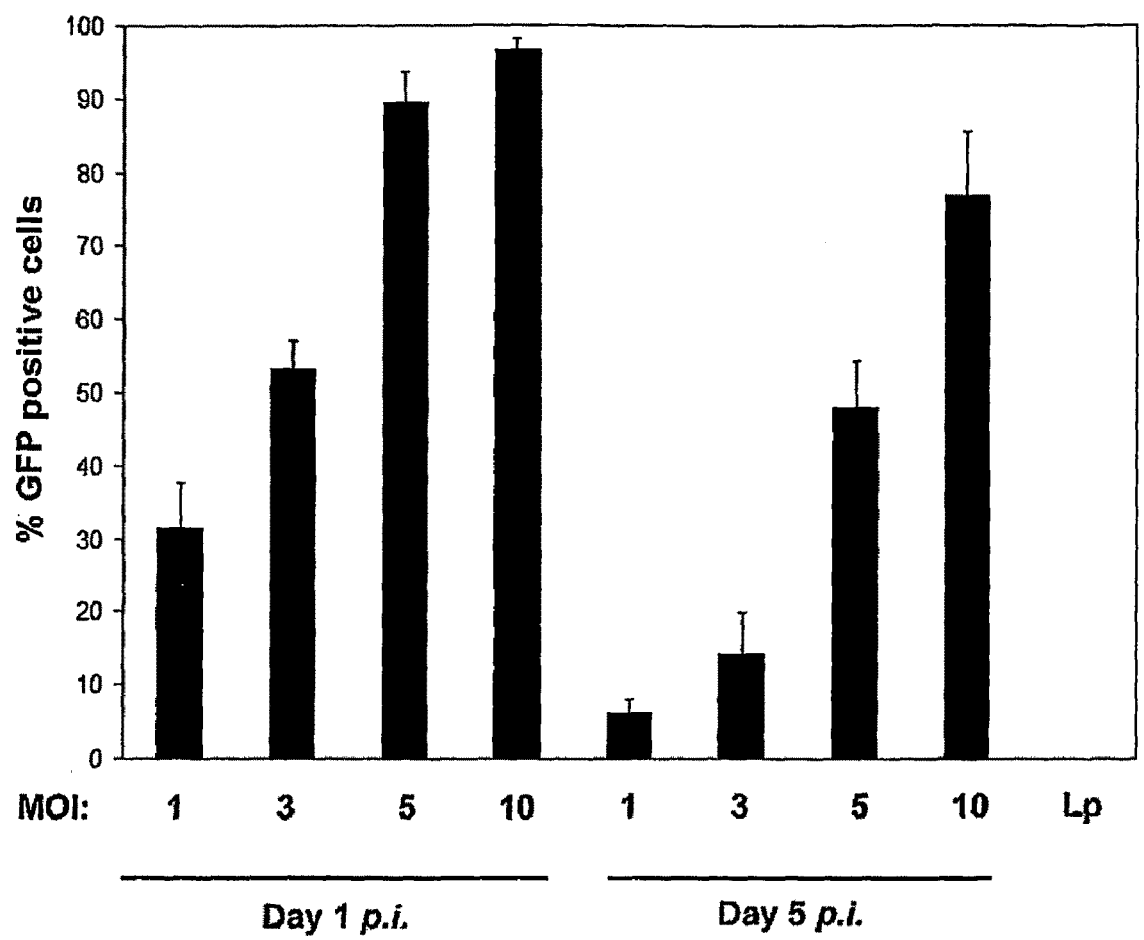

Flow cytometric analysis of RAW cells infected with GFP-expressing *M. smegmatis* gave a measure of the efficiency of bacterial uptake by the cell line. As expected, RAW macrophage cells were very efficient at taking up *M. smegmatis* (FIG. 2C). At a multiplicity of infection (MOI) of 10 bacteria per cell, a mean of 96.5±1.65 percent of the RAW cell population had phagocytosed one or more bacteria after 24 hours (FIG. 2D). This number decreased over time, reflecting bacterial killing by the host cells, although the number and intensity of fluorescing RAW cells was observed to increase over time. This may reflect a lag in plasmid delivery to the nucleus and subsequent expression by the cell, or imply that bacterial destruction facilitates DNA release into the cell.

Despite the low frequency of GFP expression observed in RAW cells infected with *M. smegmatis* bearing pYUB1083, this number was comparable to that observed in transfections using pYUB1083 DNA and lipofectamine, a highly optimized reagent for DNA transfer (0.0385%±0.009) (FIG. 2D). This demonstrates that despite a high efficiency of bacterial uptake, RAW macrophage cells are a very inefficient model for studying bactofection.

Figure 3:
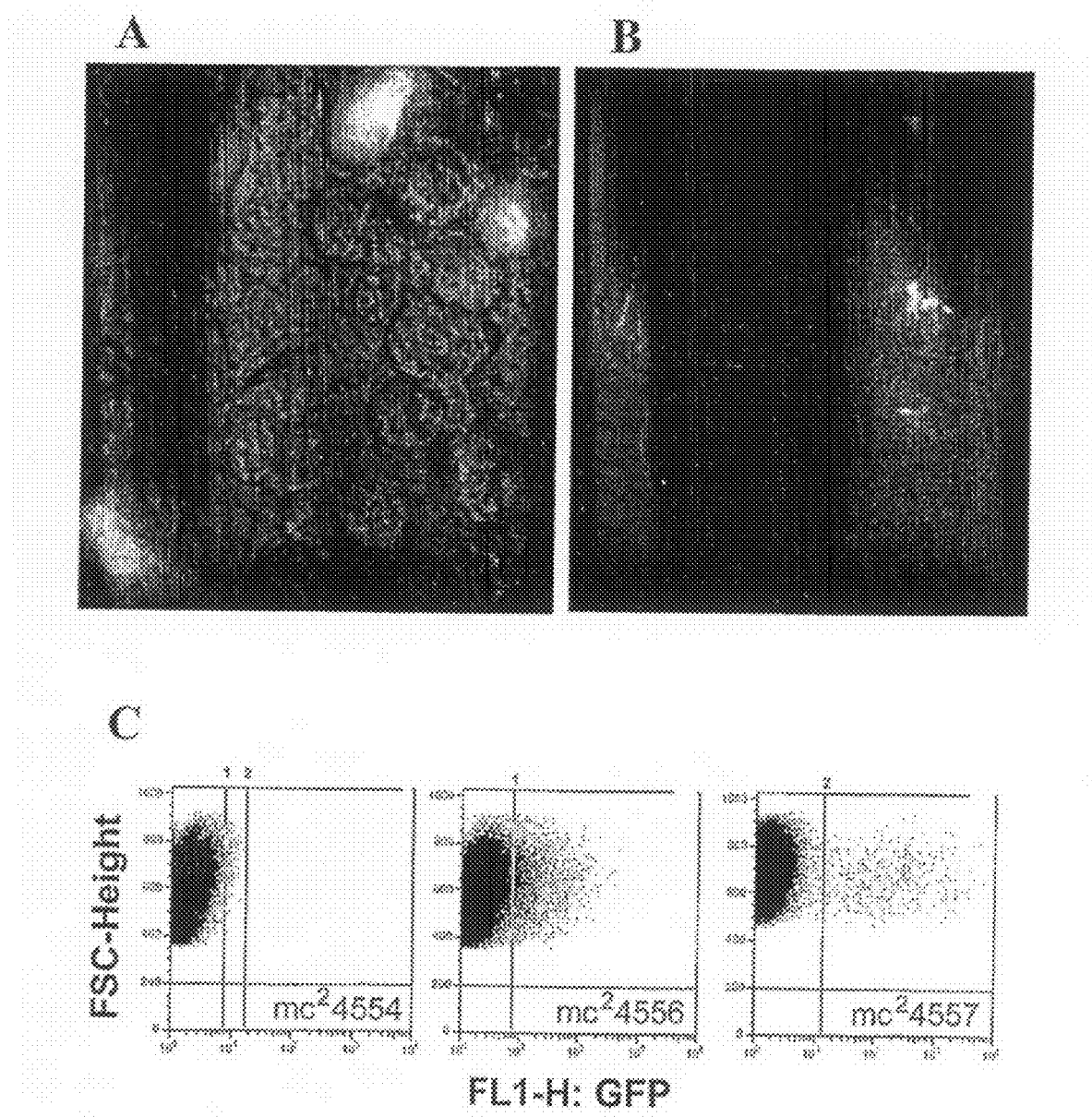
FIG. 3 is florescence micrographs and graphs showing GFP expression by *M. smegmatis* and infected HeLa cells. HeLa cells were infected with mc$^2$4557 (Panel A) or mc$^2$4556 (Panel B) at an MOI of 100 and observed under fluorescence microscopy after 24 hours. Original images taken at 40× magnification. HeLa cells infected with mc$^2$4554, mc$^2$4556 or mc$^2$4557 at an MOI of 50 were also collected five days post infection for flow cytometric analysis. Charts representative of a minimum of three experiments are displayed, with quadrant axes aligned to reduce background in high percentage (1) and low percentage (2) GFP-expressing samples (Panel C). The percentage of GFP expression seen in mc$^2$4557 infections can also be adjusted to reflect only the percentage of cells that have internalized bacteria, as measured by GFP expression from mc$^2$4556-infected cells at the earliest time point (Day 1 has 14.0±7.42% GFP expression for an MOI of 50. 0.477/0.14=3.4). HeLa cells were infected with Mc$^2$4556 at an MOI of 1, 3, 10, 50, or 100, or 10 μg of pYUB1083 DNA with lipofectamine (Lp). Cells were collected 1 or 5 days post infection and analyzed by flow cytometry (D).
Figure 3D:
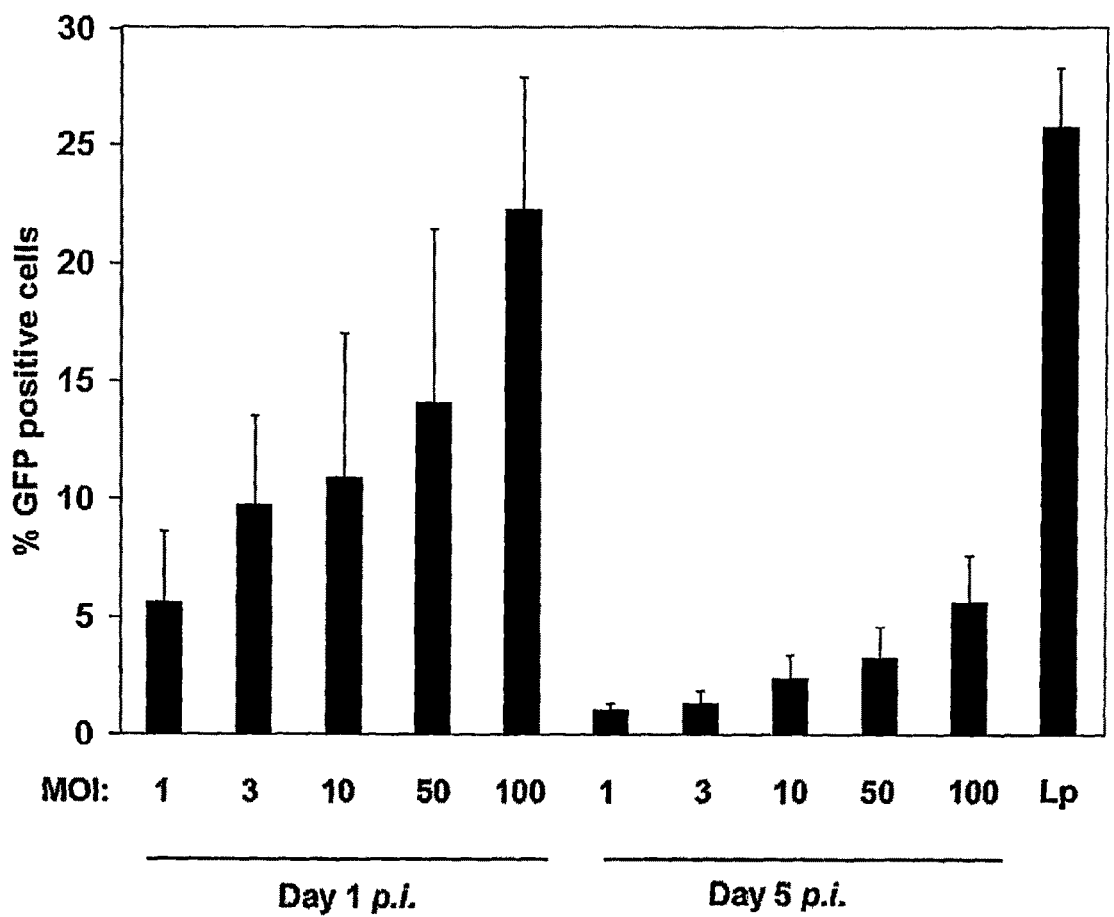

Delivery of reporter plasmids to a human carcinoma cell line with *Mycobacterium smegmatis* and *Mycobacterium bovis* BCG. HeLa cells, derived from a human cervical carcinoma, have been shown by other studies to have a high transfection efficiency using lipofectamine and GFP plasmids (Grillot-Courvalin et al. 2002). When this cell line was infected with *M. smegmatis* bearing pYUB1083, a significantly higher proportion of HeLa cells than RAW cells expressed GFP at the same MOI, implying a more successful rate of gene transfer (FIGS. 3B, C, D). Interestingly, this result was observed despite the lower efficiency of HeLa cells at taking up bacteria. Upon infection of HeLa cells with mc²4556, fluorescent mycobacterial rods were often observed floating outside the cells, with few appearing either intracellular or attached to the cell membrane. If one were to calculate the percentage of GFP expression in only the population of HeLa cells that carried one or more internalized bacteria, the number increases to 0.477±0.204 percent. This number can be further increased by raising the MOI to 100, which helps to compensate for the lower bacterial uptake of HeLa cells. Lipofectamine mixed with $10^{-5}$ grams of pYUB1083 plasmid DNA added to HeLa cells resulted in a high percentage of GFP expression (25.8±2.5%). However, each infecting dose of *M. smegmatis* measured for an MOI of 10 carries an equivalent of only $7.21 \times 10^{-11}$ grams of plasmid DNA. This demonstrates the significantly improved efficiency of gene transfer using bacterial delivery systems instead of DNA alone.

Figure 4:
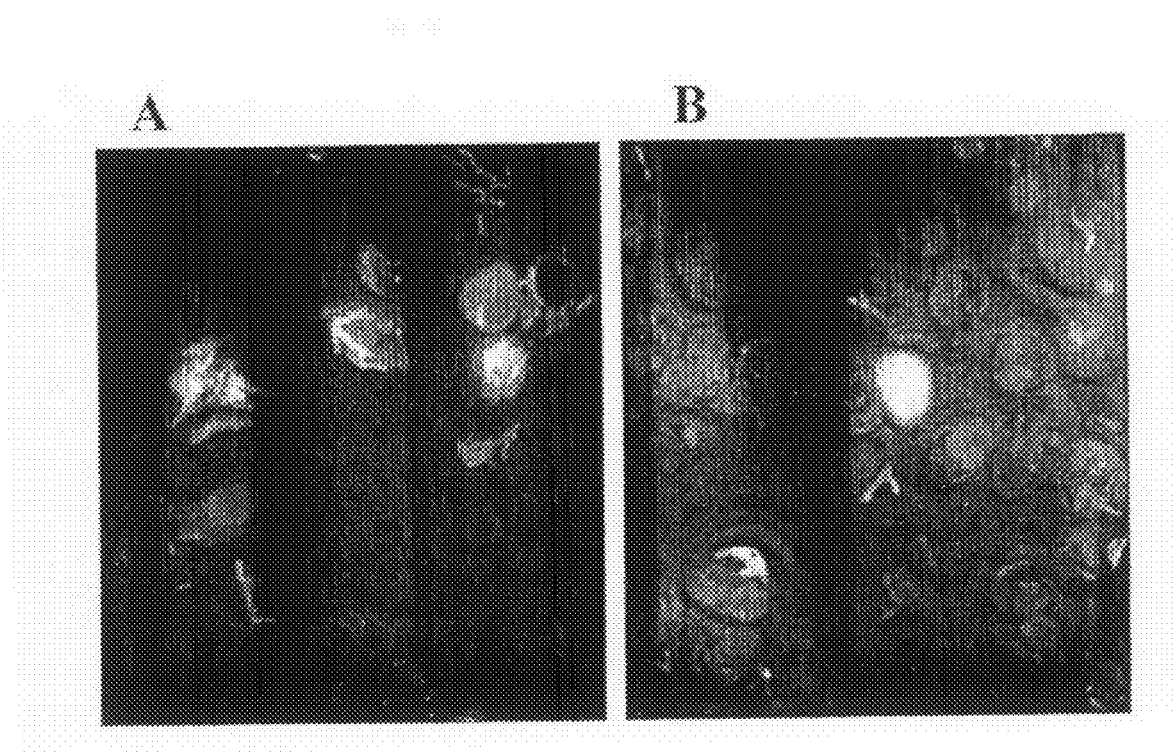
FIG. 4 is fluorescence micrographs correlating bacterial burden with RAW cell GFP expression. RAW cells were infected with *M. smegmatis* mc$^2$4559 at an MOI of 10. Different samples of fluorescing RAW cells and mycobacteria were observed under microscopy 24 hours post infection (Panel A), and with one sample stained with violet DNA dye to highlight the nucleus (Panel B). Images combine and enhance emissions recorded using red, green, and violet filters.

In an attempt to correlate the level of bacterial uptake with the successful expression of GFP by the cell, a plasmid was created that encoded two different fluorescent proteins fused to mycobacterial or eukaryotic promoters. This plasmid, pYUB1085, includes both the dsRed2 gene under the control of the *Mycobacterium marinum* msp12 promoter and egfp under the eukaryotic CMV promoter. By microscopy, it is apparent that cells with as few as one or two internalized bacteria are able to transfer the plasmid to RAW or HeLa cells to permit GFP expression (FIG. 4).

Figure 5:
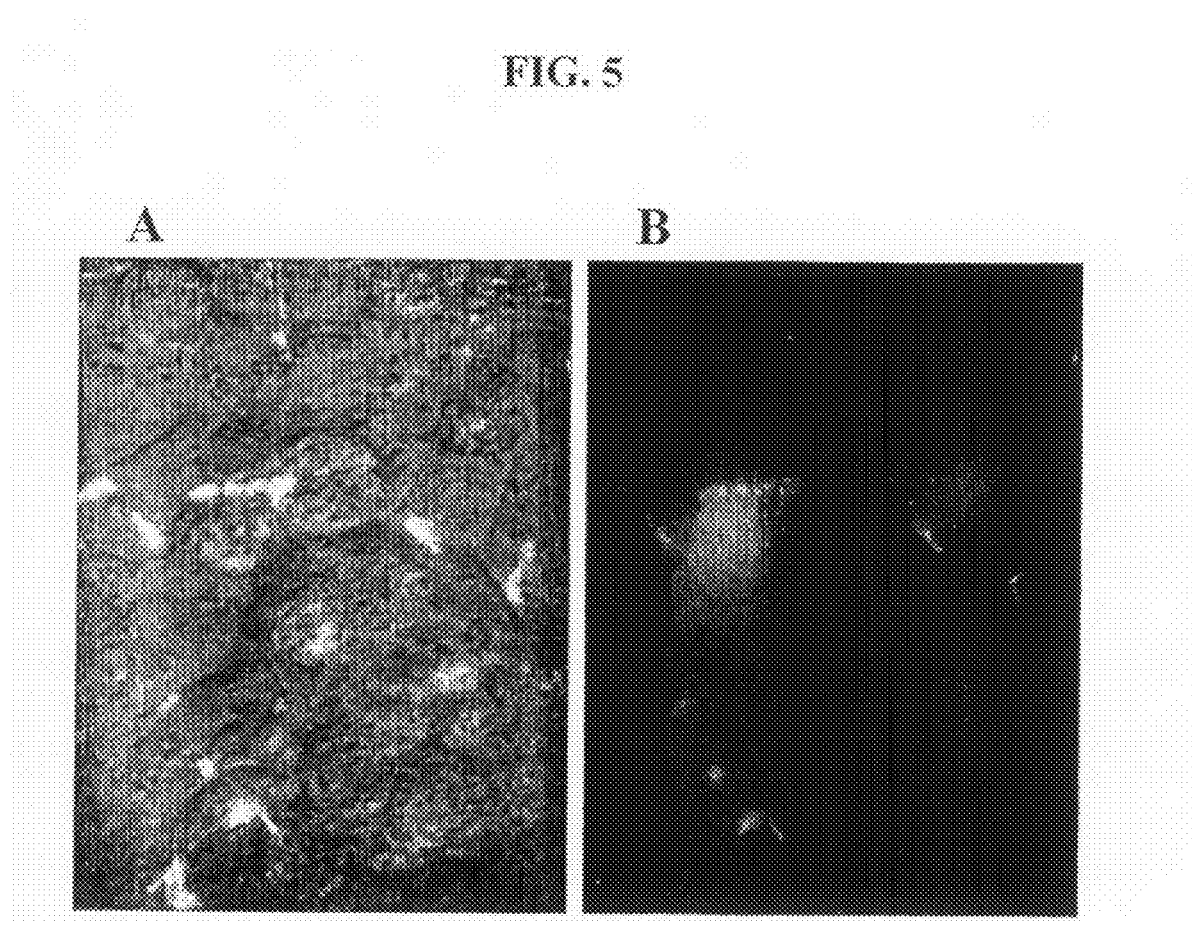
FIG. 5 is fluorescence micrographs correlating bacterial burden with HeLa cell GFP expression. HeLa cells were infected with *M. smegmatis* mc$^2$4559 at an MOI of 100. Fluorescing mycobacteria and HeLa cells were observed under microscopy 24 hours post infection. Images combine phase contrast and red filter fluorescence (Panel A) or red and green fluorescence (Panel B). Original images taken at 40× magnification.

To test whether *M. bovis* BCG was also capable of bactofection, the Pasteur laboratory strain was transformed with mycobacterial and eukaryotic GFP expression plasmids and used to infect HeLa cells. The strain carrying the pYTB1082 plasmid (mc²4581) demonstrated that HeLa cells take up BCG (FIG. 5B) at rates slightly higher than what is observed with *M. smegmatis* (FIG. 2D). GFP expression was detected in HeLa cells infected with BCG Pasteur carrying pYUB1083 (mc²4582), albeit at lower levels than what was seen with *M. smegmatis* strains (0.021%±0.004) (FIG. 5A).

Plasmid transfer with lysis-susceptible mycobacteria. Enhanced plasmid transfer efficiency has been observed in auxotrophic mutants of other bacterial species used to study bactofection. These mutant strains prematurely lyse due to the absence of specific nutrients inside the cell. To test whether mycobacteria also show improved levels of gene transfer when bacterial lysis is induced, auxotrophic mutants of *M. smegmatis* and *M. bovis* BCG were transformed with the GFP expression plasmids.

Figure 6:
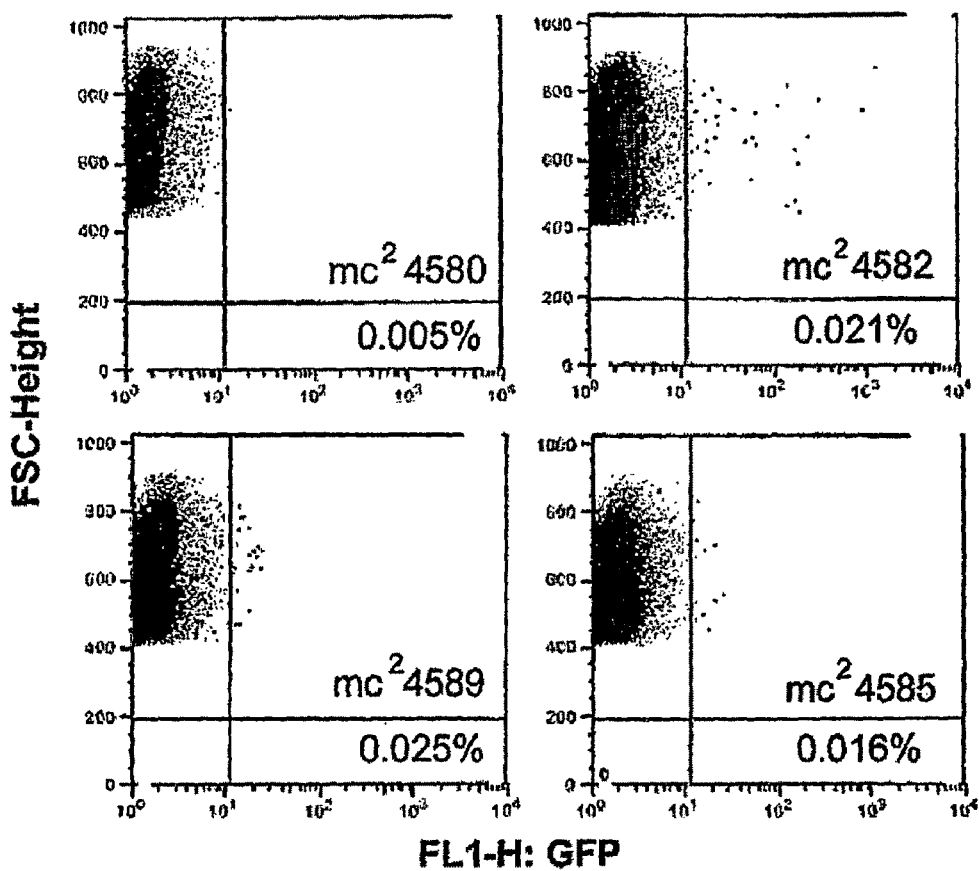
FIG. 6 is graphs showing bacterial uptake and efficiency of gene transfer to HeLa cells by *M. bovis* BCG. HeLa cells were infected with Pasteur BCG carrying pMV261 (mc$^2$4580), or Pasteur BCG or auxotrophic strains of BCG carrying a P$_{CMV}$::gfp plasmid (Panel A) or P$_{hsp60}$::gfp plasmid (B) at an MOI of 100. Cells were analyzed by flow cytometry for GFP expression 24 hours post-infection. Percentages are representative of one out of a minimum of three experiments.
Figure 6:
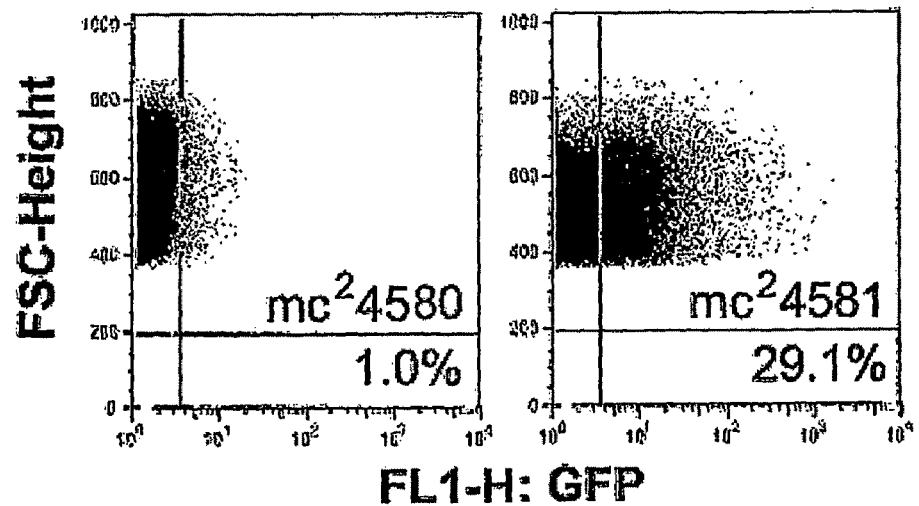

Both RAW cells (data not shown) and HeLa cells infected with these strains failed to show improved gene transfer compared to wildtype groups (FIG. 6). Likewise, infections taking place in the presence of the drug isoniazid, which inhibits cell wall synthesis and causes bacterial lysis after a few generations, did not lead to significant differences in GFP expression in infected cells. Therefore, early lysis of mycobacteria does not appear to improve the delivery of DNA into the host cell.

Plasmid transfer with conjugation mutants of *M. smegmatis*. A possible mechanism by which *M. smegmatis* releases plasmid DNA to host cells is through its conjugation system, which mediates DNA transfer to other mycobacteria (Parsons et al. 1998). Transposon insertion mutants in and around the RD1 region of the chromosome can lead to a hyperconjugation phenotype (Flint et al. 2004). These insertions appear to interrupt the function of genes that play a role in suppressing conjugation, perhaps via the decreased expression of the Cfp10 and Esat6 proteins encoded by this region. In addition, Flint observed that when the mutants are complemented with the RD1 region of *M. tuberculosis*, the hyperconjugative phenotype is reduced or eliminated completely. By contrast, insertions in the gene encoding lipoprotein LpqM (Ms4898) caused a severe reduction (1000×) in conjugation ability (Derbyshire, unpublished).

Figure 7:
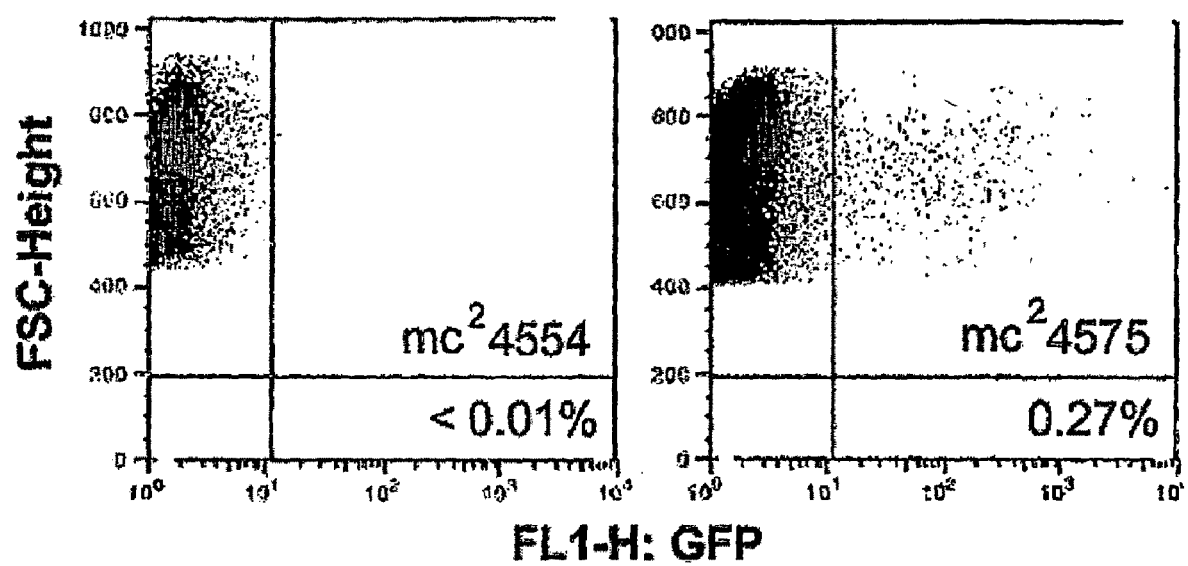
FIG. 7 is graphs showing GFP expression by HeLa cells infected with a DAP auxotroph of *M. smegmatis*. HeLa cells were infected with mc$^2$4575 at an MOI of 100 and collected 4-5 days post infection for flow cytometric analysis. Percentages are representative of a minimum of three experiments.
Figure 8A:
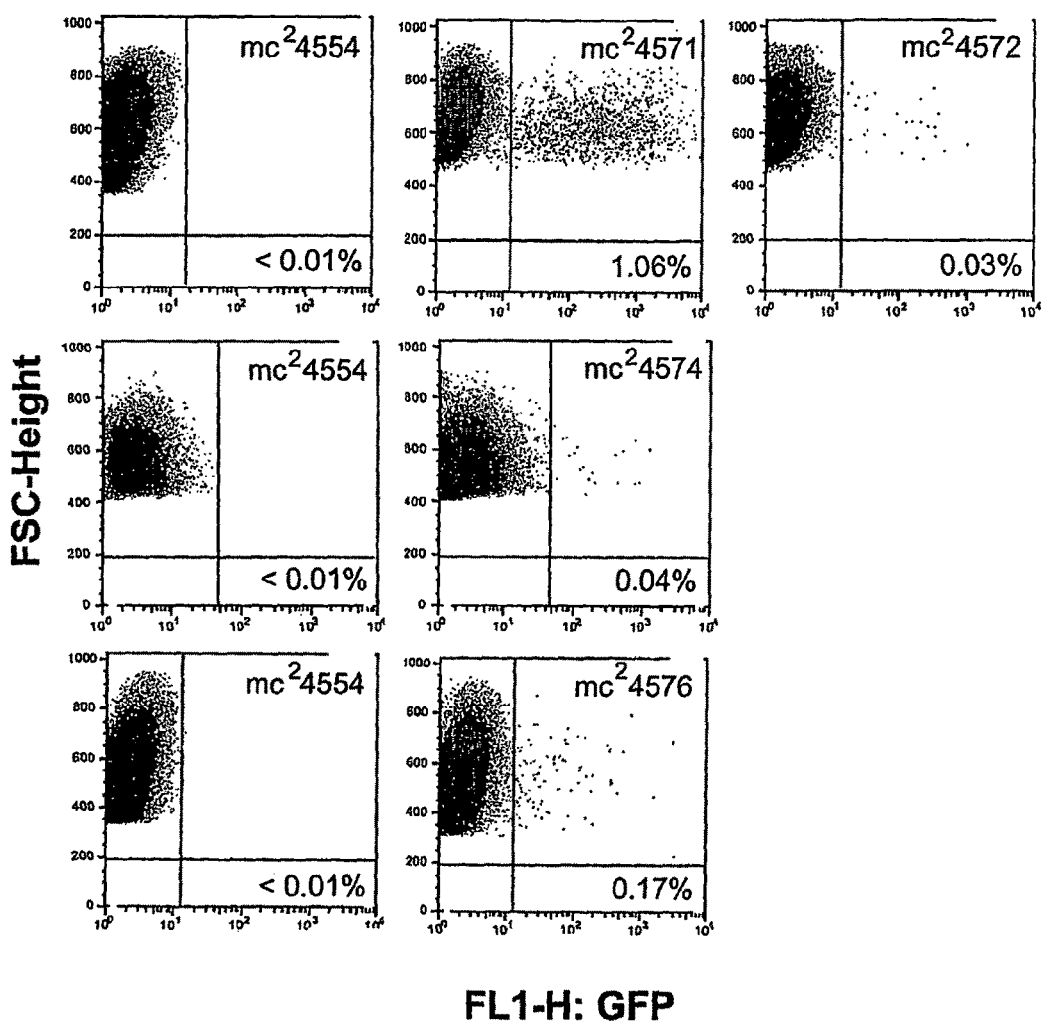
FIG. 8 is graphs showing the efficiency of gene transfer to HeLa cells by conjugation mutants of *M. smegmatis*. HeLa cells were infected with mc$^2$4554, mc$^2$4571, mc$^2$4572, mc$^2$4574 or mc$^2$4576 at an MOI of 50 and collected 4-5 days post-infection for flow cytometric analysis (Panel A). To directly compare the efficiency of the hyperconjugating mutant with wildtype *M. smegmatis*, HeLa cells were infected with mc$^2$4554 (1), mc$^2$4557 (2) or mc$^2$4571 (3) at an MOI of 100 and collected 4-5 days post-infection for flow cytometric analysis (Panel B). Student's t-test was used to calculate significance between GFP expression in cells infected with mc$^2$4557 versus mc$^2$4571; P=0.04. Percentages are representative of a minimum of three experiments.
Figure 8B:
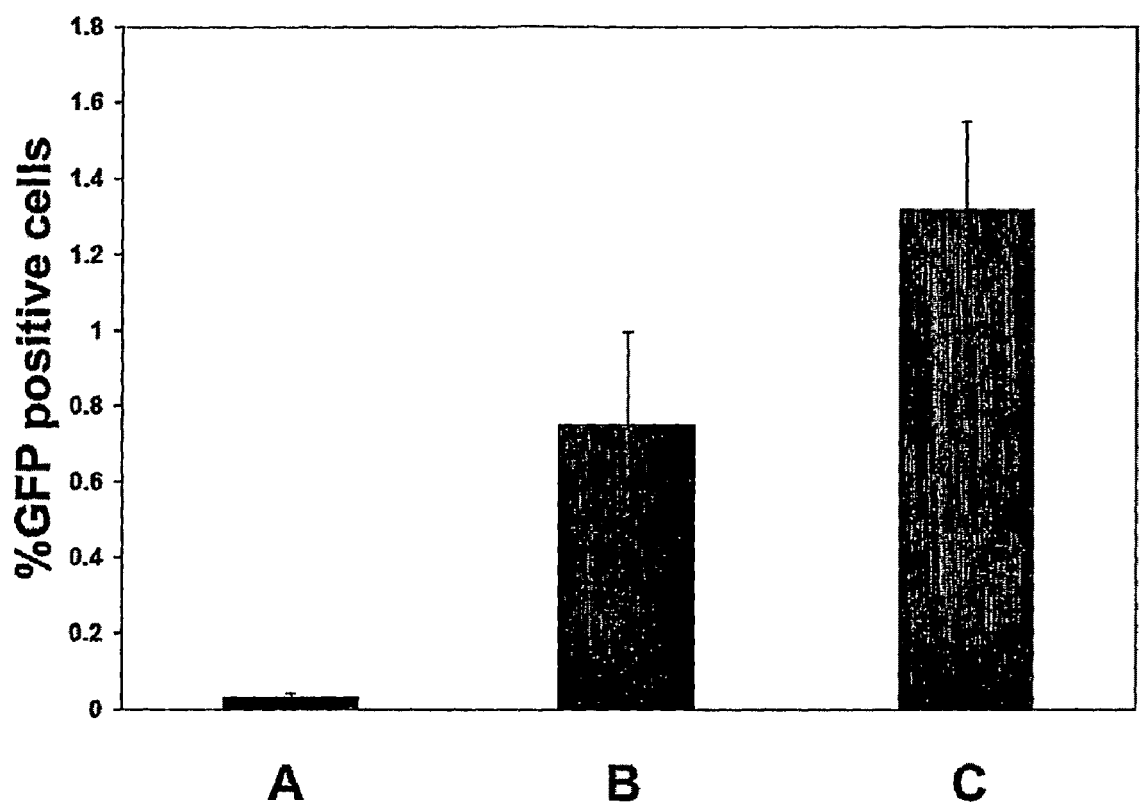

To test whether enhanced conjugation also leads to improved rates of bactofection in infected eukaryotic cells, the mKD211 hyperconjugation mutant (mc²4571) and the hypoconjugating mutant (mc²4574) were transformed with pYUB1083. It was found that HeLa cell infections with mc²4574 resulted in significantly higher (P=0.04) levels of GFP expression than wildtype strains (FIG. 7). Complementation of the mKD211 mutation (mc²4572) severely decreased its ability to transfer the pYtB1083 plasmid to infected cells. Although it was expected that the "hypoconjugating" mutant would demonstrate almost no bactofection ability, low levels of GFP expression were still detected in HeLa cells infected with this strain. An *M. smegmatis* mutant with the entire esat6-cpf10 region of RD1 deleted was also transformed with pYUB1083 (mc²4576), however this strain did not demonstrate any increase in DNA transfer over wildtype strains. These different phenotypes suggest that the mutants affect conjugation and bactofection differently, and that these two processes are regulated or mediated by separate pathways.

Delivery of Influenza DNA vaccines to mice via mycobacteria. Plasmids encoding the hemagglutinin (HA), the major surface glycoprotein of the virus, induces both humoral and cellular immunity against mouse Influenza. Immunized mice displayed a significant increase in survival and reduced lung titers of virus after challenge (Bot et al. 1997). Therefore, the HA gene was selected for cloning into a mycobacterial shuttle plasmid, under the control of the CMV promoter, to produce the DNA vaccine vector, pYUB2406.

Wildtype M. smegmatis and M. bovis BCG, as well as temperature-sensitive and auxotrophic strains and a hyperconjugating M. smegmatis mutant, were transformed with the HA plasmid and administered to mice via intravenous (i.v.), intranasal (i.n.), subcutaneous (s.c.) and/or intradermal (i.d.) routes in four immunizations, three to four weeks apart. Mice were also immunized with controls that included the attenuated Influenza virus and direct intramuscular injections of the plasmid DNA.

Mice were challenged with wildtype virus a month after the last boost. The $LD_{50}$, which is the lethal dose that kills fifty percent of the population, is estimated to be around $10^3$ pfu for Influenza A/WSN/33. As the efficiency of DNA delivery observed by mycobacteria in vitro was not very high, it was difficult to select a challenge dose estimated to be high enough to produce visible differences between experimental and control groups, but not so high as to overpower a potentially weak immune response and mask the protective effect of the vaccine. The $LD_{100}$ has been extrapolated to range between $10^5$ and $10^6$ pfu, therefore a dose of $10^4$ pfU was initially selected. However, due to loss of virus viability in transport or errors in calculating the viral titer, it was often discovered that mice had been over- or under-challenged with virus. Samples used for challenge were later retitrated and found to be different than what had originally been measured.

The attenuated Influenza D2A strain conferred 100% survival to mice at a challenge of as high as $10^6$ pfu of wildtype virus. By contrast, mice injected with PBS displayed no survival at a challenge dose of $10^4$ pfu and above, but 100% survival at $10^2$ pfu. Mice immunized intramuscularly with the pYUB2406 DNA plasmid alone consistently conferred between 60-100% survival to challenged mice.

Mycobacterial vaccines delivering pYUB2406 resulted in improved levels of survival in mice compared to PBS controls, especially when administered intranasally, however the efficiency is difficult to assess. Varying levels of protection were observed depending on the dose of challenge virus, with Mycobacteria carrying empty plasmids occasionally inducing protection as well. This was not entirely unexpected, as BCG alone had previously been found to protect mice from Influenza infection through nonspecific stimulation of cell-mediated immunity, especially via the intranasal route (Spencer et al. 1977).

Figure 9:
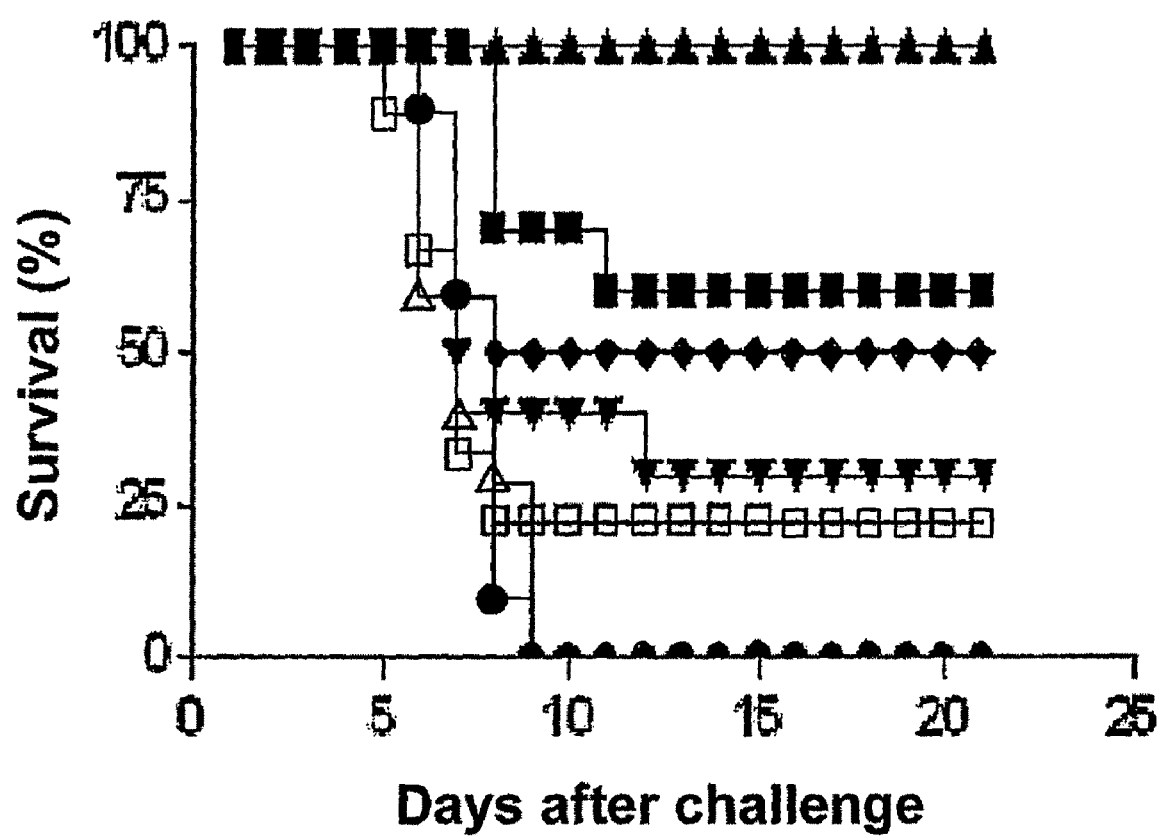
FIG. 9 Survival in immunized mice after a lethal intranasal influenza A/WSN/33 challenge. Groups of 8 to 10 mice were immunized with attenuated influenza D2A/WSN/33 virus (▲), i.m. pYUB2406 (■), *M. smegmatis* mc$^2$4562 harboring pYUB1090 (♦), *M. smegmatis* mc$^2$4562 harboring pYLTB1060 (Δ), *M. smegmatis* mc$^2$155 harboring pYUB2406 (▼), *M. smegmatis* mc$^2$155 harboring pMV261 (□), or PBS (●). Mice were challenged one month after the last immunization with 10$^5$ pfu of wild-type influenza A/WSN/33 virus. Differences in survival among hyperconjugating strains was measured as significant (P=0.02), but not between wildtype mc$^2$155 *M. smegmatis* strains.

Initial experiments assessed which was the best route for immunization, and whether mycobacterial lysis improved gene transfer in vivo. An isoniazid-resistant temperature-sensitive strain of M. smegmatis ($mc^2$2359) was transformed with pYLJB2406 and grown to an $OD_{600}$ 0.2, then shifted to 42° C. for three hours before injection into mice. The growth kinetics of this mutant were previously studied and show that cfu counts begin to drop at this time point (Vilcheze et al., 2000), marking the onset of lysis. Mice were injected intranasally, intravenously, or primed intranasally and boosted intravenously with this strain. Upon challenge, it was found that mice immunized solely by i.v. injection were not protected (0% survival), while priming first by i.n. injection gave 14% survival, and mice receiving four intranasal injections showed 40% survival (FIG. 9). However, the non-lysing control strain showed comparable levels of immunization, even when it carried the empty pMV261 plasmid, most likely due to nonspecific immune stimulation by the mycobacteria itself. Interestingly, even in the negative control, the highest level of survival was seen in mice immunized intranasally. This confirms the importance of mucosal immunizations in protecting against Influenza and other respiratory viruses (Ul-mer et al., 2002). Studies comparing protection against HSV with DNA vaccines administered via different routes in a prime-boost system have also shown that mucosal antibody and T cell responses are only present if at least one immunization is given at a mucosal site (Eo et al., 2001)

Similar to the above experiment, the $mc^2$ 155 strain of M. smegmatis carrying pYUB2406 was heated to 65° C. for five minutes before injection, to weaken the integrity of the cell wall and induce lysis. Comparable levels of infection were observed between samples that had been heat-shocked and those that were not, and between strains that carried pYUB2406 or the empty pMV261 plasmid. The subcutaneous route of injection was also tested for a potential improvement in immunization, but it showed similar or slightly decreased levels of protection compared to intranasally immunized mice.

Although auxotrophic strains of Mycobacteria showed no improvement in the delivery of GFP plasmids for expression in vitro, a lysine auxotroph ($mc^{211604}$) and pantothenate auxotroph ($mc^2$6000) of BCG were tested for their ability to deliver pYUB2406 in vivo compared to the laboratory Pasteur strain. In agreement with the in vitro studies, mice immunized with these strains showed no improvement in protection compared to Pasteur BCG, which itself conferred levels of protection similar to M. smegmatis. Similar to what was observed with M. smegmatis, BCG strains also induced a high level of nonspecific protection, as measured by the survival of mice immunized with negative control strains carrying pMV261. In the BCG lysine auxotroph $mc^2$1604, however, the effect of the background immunization decreased with increasing doses of viral challenge. This effect would be expected if nonspecific immunization by the mycobacterial vector induced only limited protection, and against high doses of viral challenge, specific immunization against hemagglutinin was required for improved survival. This creates a very small margin for error when calculating the challenge dose, however. Experiments where virus was incorrectly titrated and mice were challenged with $10^6$ pfu of Influenza resulted in the death of 90-100% of all Mycobacteria-immunized mice.

With the failure of lysis models to show improved DNA vaccine transfer to mice, it was hoped that hyperconjugating mutants would follow the same trend observed in vitro and demonstrate superior Influenza immunization compared to wildtype M. smegmatis. The hyperconjugative M. smegmatis mutant $mc^2$4562 was transformed with a derivative of pYUB2406 (pYUB1090) and administered to mice in four intranasal injections, three weeks apart. These mice showed 50% survival after challenge one month after the last boost with $10^5$ pfu of virus, whereas the clone carrying the empty vector (pYUB1060) conferred no protection, resulting in 0% survival. In comparison, M. smegmatis $mc^2$155 carrying pYUB2406 conferred 30% survival to challenged mice, although the clone carrying the empty vector induced nonspecific protection and showed 20% survival in that group.

To confirm the improved protection observed in mice immunized with $mc^2$4562, the hyperconjugating mutant was tested once more for its ability to deliver the Influenza DNA vaccine, this time alongside S. flexneri 15D for comparison. Once again, immunizations with the hyperconjugating mutant resulted in 50% survival in mice receiving the strain carrying the HA-plasmid, and 0% survival in mice with M. smegmatis carrying the empty vector. The auxotrophic 15D mutant carrying a pYUB2406 derivative (pYUB1089) conferred fall protection and 100% survival to challenged mice, although it also induced nonspecific protection and 30% survival in mice immunized with the strain carrying pYUB1060.

To assay for specific protection against Influenza A/SN/33, serum was collected from mice after each immunization and immediately prior to challenge. ELISAs were performed in plates coated with whole virus particles, using detection antibodies specific for total IgG, IgM and IgA. No Influenza-specific antibodies were detected in the sera of mice immunized with any of the mycobacterial strains, although low levels of Influenza-specific serum IgG and mucosal IgA were detected in mice immunized with Influenza D2A, pYUB2406 DNA, and *S. flexneri* 15D-pYUB2406 (Vecino et al. 2004). Mice that received the naked DNA vaccine or the attenuated flu strain showed high numbers of IFB-γ-producing T cells among recovered splenocytes, whereas lower but significant ($P<0.05$) levels of IFN-γ-producing T cells specific against Influenza were recovered from mice immunized with *S. flexneri* and *M. smegmatis* strains harboring the hemagglutinin-encoding plasmid (Table 2). No Influenza-specific IFN-γ responses or spontaneous release of IFN-γ were detected from groups immunized with the empty plasmid or PBS.

TABLE 2

Frequency of influenza-specific ifh-γ responses among splenocytes recovered from Balb/c mice

| Vaccine | Route of immunization | Spot forming units per million splenocytes |
| --- | --- | --- |
| pYUB2406 | i.m. | 349 ± 14.17 |
| D2A/WSN/33 | i.n. | 185 ± 11.53 |
| PBS | i.n. | 0 |
| mc²155 pYUB2406 | i.n. | 21.7 ± 0.58 |
| mc²155 pMV261 | i.n. | 0 |
| mc²4562 pYUB2406 | i.n. | 26.7 ± 1.53 |
| mc²4562 pMV261 | i.n. | 0 |
| 15D pYUB2406 | i.n | 20 ± 2.08 |
| 15D pMV261 | i.n | 0 |

The production of both an antigen-specific humoral and cell-mediated response in mice injected intranasally with the 15D-pYUB2406 strain is in agreement with what has been observed in studies using *S. flexneri* to intranasally deliver DNA vaccines against HIV and measles (Vecino et al. 2002). The absence of a detectable humoral response in mice injected with the hyperconjugating *M. smegmatis* strain was surprising, because mc²4562 had conferred significant protection to immunized mice. Because the ELISA assay does not specifically look for neutralizing antibodies in the serum samples, a more sensitive test was used to measure anti-HA antibodies in these groups. The hemagglutination inhibition assay quantifies the level of antibodies against HA by examining their ability to bind to the antigen and inhibit its ability to agglutinate red blood cells. However, despite a measurable hemagglutinin inhibition (HI) effect being present in serum from DNA and attenuated influenza immunized mice, serum from *Mycobacteria*-immunized mice did not display any HI activity (data not shown).

It is possible that the protection observed in mice immunized with mycobacterial strains does not require an elevated humoral response. Studies with DNA vaccines encoding Influenza HA have shown minimal IgG and HI antibody production, yet resulted in a strong Th1 response and protection against challenge with the virus (Johnson et al. 2000). Interferon-γ itself may play an important role in protecting mice against Influenza by directly inhibiting its ability to multiply inside infected cells (Bot et al. 1998).

Discussion

Plasmid delivery and subsequent transgene expression by infected eukaryotic cells has now been demonstrated with *Mycobacterium smegmatis* and *M. bovis* BCG. The expression of the GFP reporter by mycobacteria is easily distinguished from the expression by host cells under microscopy, and no inherent GFP expression was observed by the bacterial strains under flow cytometric analysis.

As expected, RAW murine macrophage cells exhibited high levels of mycobacterial infection and uptake, as macrophages are their natural target and host in vivo. An MOI of 10 resulted in 96.5±1.6% of the population carrying one or more internalized bacteria. However, only 0.036±0.1% of infected cells expressed GFP encoded by the delivered plasmid, pYUB1083. This level is similar to what was observed using pYUB1083 DNA and lipofectamine, a gold standard for testing transfection efficiency (0.0385±0.01%). Therefore, RAW cells do not represent the optimal host for the analysis of bactofection with *Mycobacteria*.

HeLa cervical carcinoma cells represent a more promising system, as they have been extensively tested in other transfection assays. Lipofectamine and pYUB1083 induced 25.8±2.5% of these cells to express GFP. Bacterial uptake with this strain was very low, with only 22.3±5.6% of the population harboring one or more bacteria at an MOI as high as 100. However, as was observed in RAW cell infections, a high bacterial burden did not always correlate with successful plasmid delivery and GFP expression. Despite a lower efficiency of infection, HeLa cells expressed higher levels of GFP than RAW cells at the same MOI in infections with *M. smegmatis* delivering pYUB1083. Of the HeLa population harboring one or more bacteria, 3.4±2.8% of the cells express GFP. A study that compared the bactofection efficiencies of different bacterial species showed 10±0.6% GFP expression in HeLa cells infected with *L. monocytogenes* carrying a different GFP plasmid, whereas GFP expression was only visible in 0.85±0.41% of *S. flexneri*-infected cells and <0.01% of *Salmonella* infected cells carrying that plasmid (Grillot-Courvalin et al. 2002). The DNA construct used in their assay may also have been more efficient at being expressed in eukaryotic cells, as they observed GFP expression in 69% of the HeLa transfected with lipofectamine. This would imply that the levels of gene transfer observed in HeLa cells using *Mycobacteria* can potentially be improved by optimizing the plasmid or other conditions during bactofection. It is worth noting, also, that transfection with lipofectamine is achieved with greater than $10^5$ grams more DNA than the equivalent amount delivered by an infecting dose of *M. smegmatis*. This supports the importance and efficiency of bacterial delivery systems for gene delivery.

As the mechanism of DNA transfer between a mycobacterium and its host cell is still unknown, two mechanisms were proposed in this study: 1) lysis-mediated DNA release, and 2) active export of DNA through the conjugation system. Other intracellular bacterial species tested for DNA delivery have shown improved efficiencies when premature lysis was induced by a lysin or auxotrophic mutation. Experiments with mycobacterial auxotrophs, however, showed no improvement in GFP expression by infected cells. It is possible that premature lysis in unnecessary, as *M. smegmatis* does not escape the endosome, nor inhibit phagosome-lysosome fusion, resulting in rapid clearance from the cell. Indeed, the number of internalized bacteria decreased rapidly over five days in HeLa cells. However, this does not explain how DNA from lysed bacteria is able to escape the vacuole.

Figure 10:
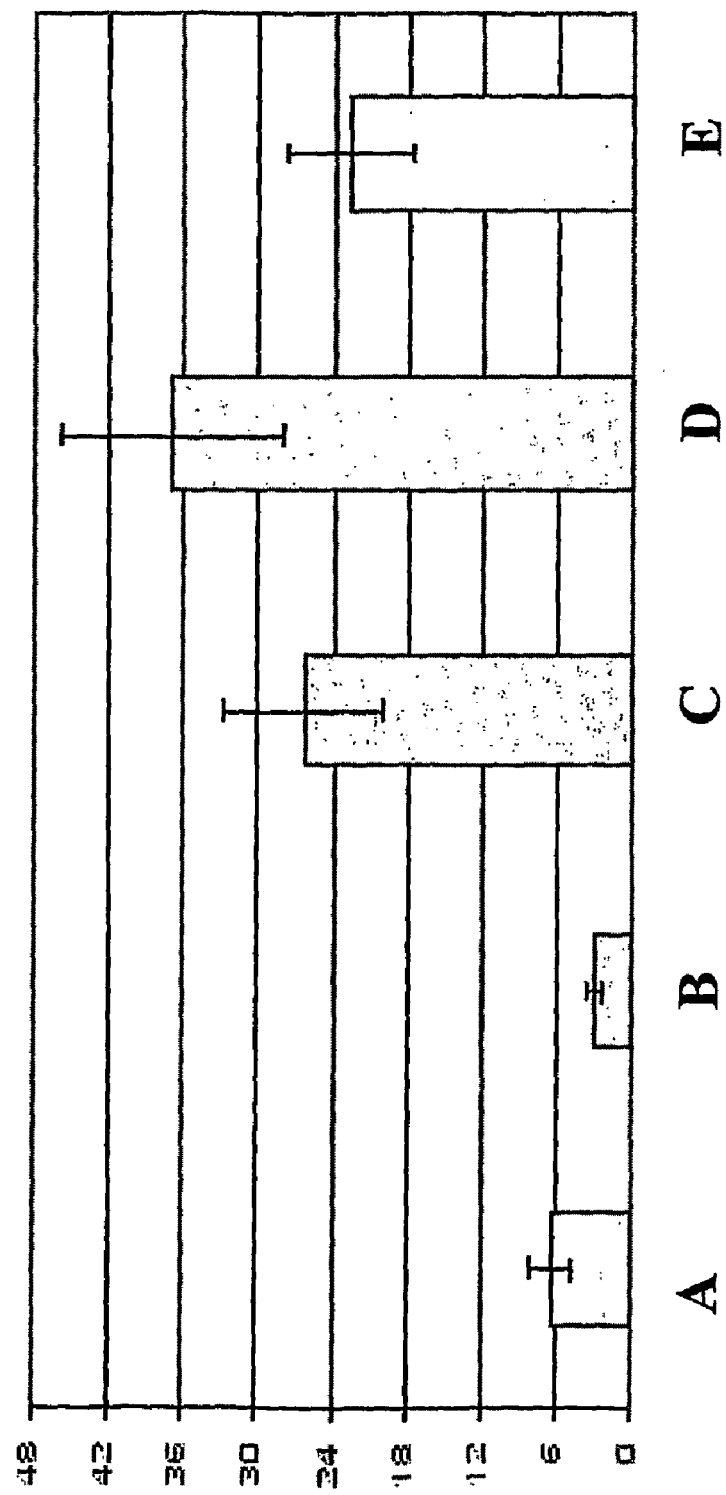
FIG. 10 is a graph showing the relative quantities of plasmid DNA recovered from 10$^{8.8}$ CFU of log phase *M. smegmatis* (A) strain mc$^2$155 (pMS116) alone OR mc$^2$155 (pMS116) harboring (B) pMV361 (to control for the effects the integrative plasmid), (C) pYM10 (D) pYM11 or (E) pYM12. Following plasmid DNA extraction (Qiagen), the intensity of total plasmid was quantified on a 0.8% agarose gel using ImageJ 1.34n software (Wayne Rasband,), after calibration using High Mass DNA ladder (Invitrogen). Since the amount of DNA and its intensity on the gel is not linearly related, calibration was required. The exact amount of DNA is already known for all six bands in the High Mass DNA ladder and the corresponding intensity of each band can be measured by ImageJ. Using these tools, a standard curve was created and the intensity of pMS116 was measured and corresponding amount of DNA was calculated based on the standard curve. The error bars indicate the ±SD from three independent experiments.
Figure 11:
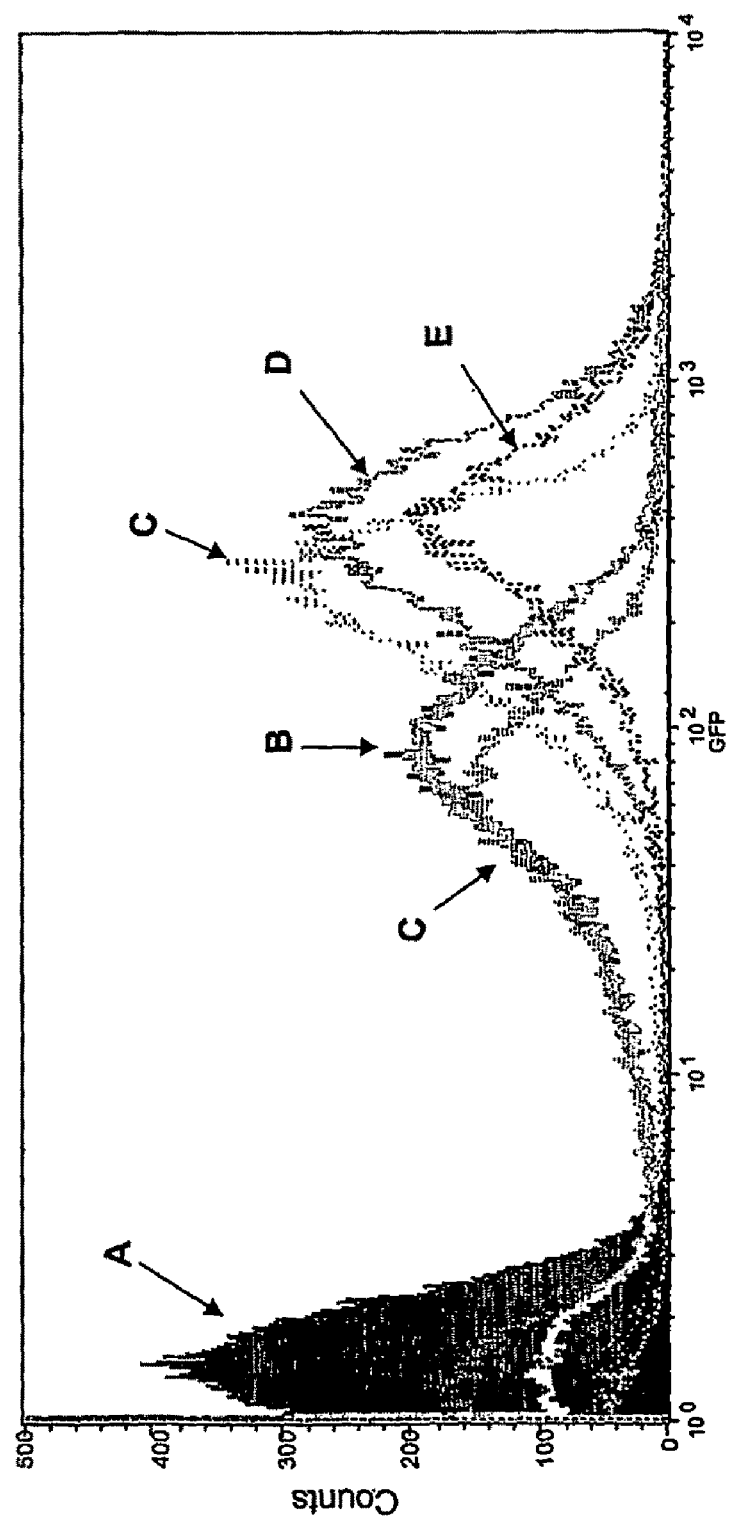
FIG. 11 is a graph showing relative intensities of GFP expression in (A) *M. smegmatis* strain mc$^2$155 alone (to control for background bacterial autofluorescence); (B) mc$^2$155 (pMS116) alone OR mc$^2$155(pMS116) harboring either (C) pMV361 (to control for the effects the integrative plasmid), (D) pYM10, (E) pYM11, or (F) pYM12. A population of 50,000 bacteria of each strain was grown to log-phase and analyzed by flow cytometry (FACScan).
Figure 12:
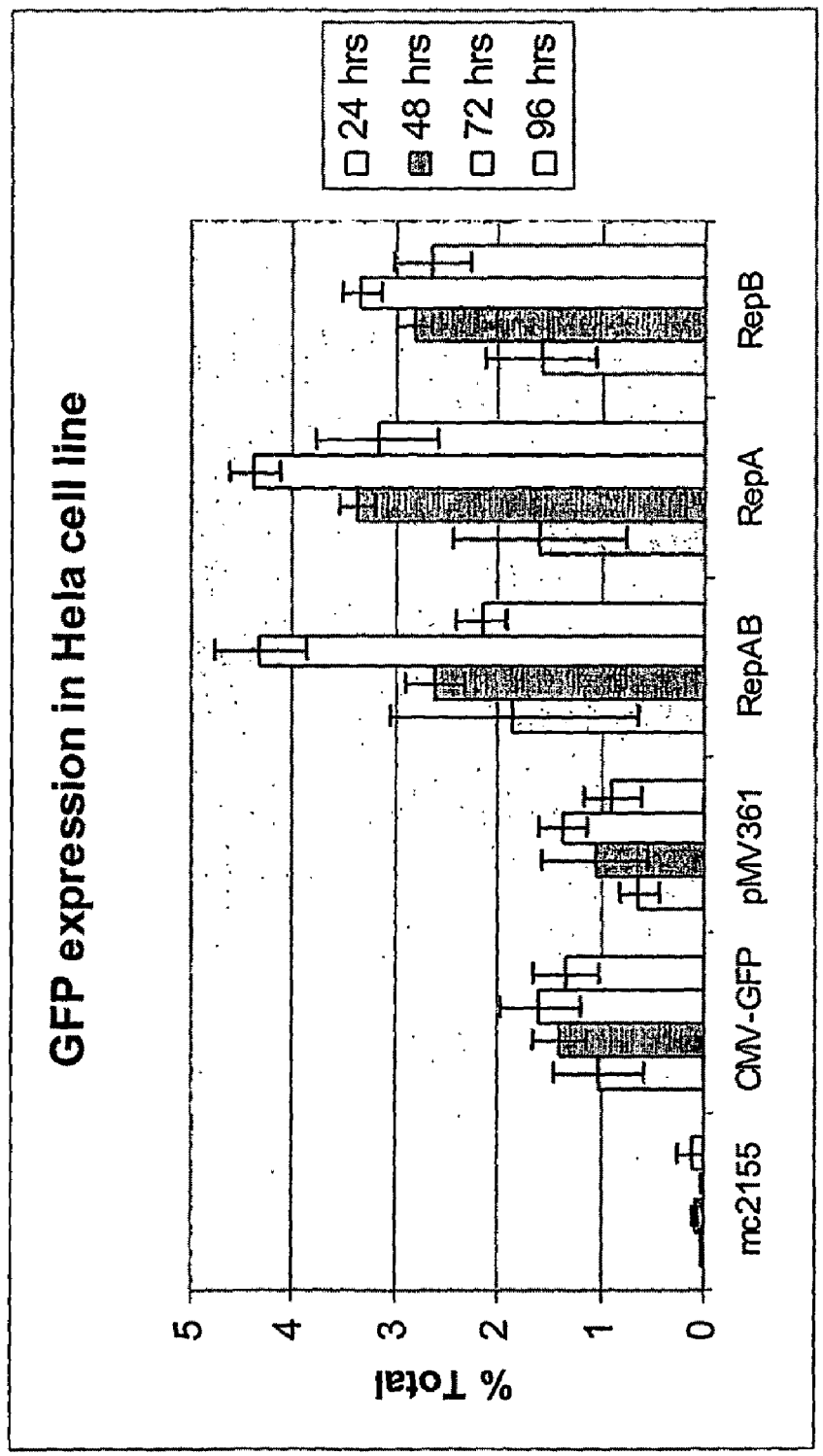
FIG. 12 is a graph showing the relative efficiency of CMV-GFP plasmid transfer to HeLa cells from (A) *M. smegmatis* strain mc$^2$155 alone (mc2155)(to control for background HeLa cell autofluorescence) (B) mc$^2$155(pMS116) alone (CMV-GFP)OR mc$^2$155(pMS116) harboring either (C) pMV361 (to control for the effects the integrative plasmid), (D) pYM10 (RepAB), (E) pYM11 (RepA), or (F) pYM12 (RepB). For each sample, the fraction of GFP expression was measured by FACS at 4 time points. Group1, mc$^2$155 showed the basic level of detectable green florescent signal; group2, mc$^2$155 harboring CMV-GFP plasmid; group3, mc$^2$155 with pMV361 harboring CMV-GFP plasmid; group4, mc$^2$155 with pMV361::RepAB harboring CMV-GFP plasmid; group5, mc$^2$155 with pMV361::RepA harboring CMV-GFP plasmid; group6, mc$^2$155 with pMV361::RepB harboring CMV-GFP plasmid. HeLa cells were cultured in a tissue culture flask in DMEM supplemented with 10% FBS, 5% NCTD-109 and 2% Hepes at 37C a 5% $CO_2$ atmosphere, seeded in 46-well culture plates at density of 10$^4$ cells per well, then infected by 5×10$^5$ CFU of each strain of mc$^2$155 and incubated 37C for 4 hours. To remove extracellular *M. smegmatis*, HeLa cell suspensions were washed ×2 with media then treated with 50 μm/ml gentamycin. To determine the proportion of HeLa cells expressing GFP, aliquots of HeLa cells were harvested at, 24, 48 and 72 and 96 hours after infection, resuspended in PBS and analyzed by flow cytometry (FACScan).

Another potential mechanism for DNA transfer to host cells is through the conjugation system, which normally directs DNA transfer to other mycobacteria. Hyperconjugating transposon insertion mutants of *M. smegmatis* had already been identified (Flint et al. 2004) and provided the ideal system to test this hypothesis. Indeed, hyperconjugating mutants showed significant improvement over wildtype strains in transfecting eukaryotic cells, and this effect disappeared upon complementation. However, mutants displaying 1000 times less conjugation than wildtype were still able to transfect cells at levels comparable to wildtype *M. smegmatis*. Although mutations altering conjugation ability might not act directly on the system that controls DNA transport, it is also possible that alternate mechanisms exist for releasing DNA to the host cell.

*M. bovis* BCG was also examined for its ability to deliver GFP plasmids to mammalian cells. BCG lacks the RD1 region and is not believed to undergo conjugation, therefore only laboratory strains and auxotrophic mutants could be tested. GFP expression was detected in cells infected with BCG strains carrying the pYUB1083 plasmid. Auxotrophic mutants displayed no significant difference in transfection efficiency.

The RD1 genes encode a secretion system and associated virulence factors in *M. tuberculosis* (Mahairas et al., 1996; Behr et al., 1999; Hsu et al., 2003; Stanley et. al, 2003). In *M. smegmatis*, which is nonpathogenic, this system is believed to have been adapted to serve different functions, and a role in conjugation is strongly inferred from the mutation of several RD1 genes and their resulting phenotype. As conjugation also involves DNA transfer between organisms, we hypothesized that DNA plasmids might be released to eukaryotic cells by the same pathway. Hyperconjugation mutants appear to improve the efficiency of gene transfer, supporting this possibility. The detection of GFP expression in cells infected with BCG and hypoconjugating mutants of *M. smegmatis*, however, infers that alternate mechanisms of DNA delivery exist.

Plasmid transfer with mycobacteria was also demonstrated in vivo through the delivery of an Influenza DNA vaccine to mice. We had previously tested this model using a *S. flexneri* carrier, and found that successful gene transfer could be measured through the production of specific humoral and cellular immune responses, as well as increased survival after challenge. The potential improvement upon current vaccines against Influenza, which remains a serious health threat, made this experiment particularly relevant.

Both *M. bovis* BCG and *M. smegmatis* induced low-level nonspecific protection against Influenza virus due to their high immunogenicity. Similar to what had been observed in vitro with GFP plasmids, auxotrophic mutants of BCG, and *M. smegmatis* induced to lyse through heat-shock or temperature-sensitive mutations, did not show an improved ability to deliver the DNA vaccine compared to wildtype strains. Interferon-γ secreting T-cells specific for Influenza virus were detected in mice immunized with *M. smegmatis* delivering the vaccine plasmid, and not in those immunized with mycobacteria carrying an empty plasmid. A significant difference in survival after viral challenge (P=0.024) between groups carrying the vaccine and the empty plasmid was only detected in mice immunized with a hyperconjugating *M. smegmatis* strain. This supports observations made in vitro that hyperconjugating mutants are more efficient at gene transfer than wildtype strains. This protection was less than what had been observed with *S. flexneri* delivering the vaccine. Mycobacterial carriers of the vaccine also failed to elicit detectable serum antibodies against the virus, which had been detected with *S. flexneri* carriers. The T cell response induced by the *Mycobacteria*-delivered vaccine may have been sufficient to mediate protection despite the absence of neutralizing IgG antibody, as had been previously described (Bot et al. 1998; Johnson et al. 2000). The protection in this group was also less than the protection conferred by the naked DNA alone. The direct DNA immunizations, however, require 1000-10,000 times more DNA molecules than the bacterial delivery systems. As this is the first recorded use of *Mycobacteria* as a delivery system for DNA vaccines, it is possible that this system can be further optimized to achieve levels of protection similar to those of the *S. flexneri*-mediated DNA vaccine.

Experiments testing different routes of vaccine injection found that intranasal immunization with mycobacteria provided the highest levels of protection compared to subcutaneous and intravenous injection. As the Influenza challenge and infection take place via the respiratory system, this result is not surprising. It is also the natural route of infection for *Mycobacteria*, which have adapted to interact with cells at this site.

In order to improve the bactofection efficiency of mycobacteria, it is important to understand the mechanism by which this species releases DNA into a host cell. Although *M. smegmatis* and BCG do not escape into the cytoplasm, successful transfection experiments with *Salmonella*, a species that also remains inside the phagosome, demonstrate that this is not necessary for gene transfer to occur in all species. Elucidation of the mechanism of DNA release by *Mycobacteria* may require the generation of new mutants through transposon mutagenesis that can be screened for improved bactofection ability. In addition, new *M. smegmatis* clones can be grown from fluorescing eukaryotic cells that are isolated by FACS sorting, with the reasoning that the bacteria that successfully transfected these cells may possess a hyper-gene transfer phenotype.

Compared to existing bacterial DNA delivery systems, mycobacteria such as *M. smegmatis* and *M. bovis* BCG have the advantage of being nonpathogenic and safe to administer to infants. BCG is already the most widely administered vaccine in the world, and is easily tolerated by the public as it can be taken orally, making it an ideal delivery system for recombinant and/or DNA vaccines against other pathogens. *Mycobacteria* have also been recognized as having strong immunomodulating properties that can enhance the immune response towards recombinant antigens or antigens encoded by the DNA vaccines it delivers to the host. As this represents the first study describing the bactofection abilities of mycobacteria, much work remains to fully characterize and optimize this system; however, it remains a promising new tool in the never-ending battle against infection.

EXAMPLE 2

Optimizing DNA Transfer from *Mycobacteria* to Host Cells

Example 1 demonstrates that recombinant nonpathogenic mycobacteria, residing exclusively in the vacuole of macrophages, can deliver eukaryotic expression plasmids to murine cell lines (including murine MB49 bladder tumor cell lines), to HeLa cells and to fresh human PBMCs. A limitation of recombinant mycobacterial vectors for gene transfer is that plasmid replication appears to be highly restricted in mycobacteria. Improved replication in mycobacteria was targeted for improvement.

Overexpression of pAL500-derived replication proteins (RepA and RepB) in *M. smegmatis* leads to an increased plasmid copy number within bacteria and an increased efficiency of plasmid gene transfer to mammalian cells. The poor mycobacterial plasmid replication in Example 1 is likely due to negative auto-regulation by RepB in pAL5000, the plasmid from which the eukaryotic expression plasmid replicons discussed in Example 1. To overcome this negative auto-regulation, pAL5000-derived RepA and/or RepB was expressed in trans in *M. smegmatis* harboring a pAL5000-based reporter plasmid that expresses eGFP from a mycobacterial promoter (designated pMS116, see Table 3). The pMS116 plasmid was equally stable in *M. smegmatis* strains expressing extra replication proteins and wild-type *M. smegmatis* grown in the absence of antibiotic selection (data not shown). A comparison of the quantity of plasmid recovered from *M. smegmatis* harboring pMS116 plus an integrative plasmid that expresses either RepA and RepB, RepA or RepB (designated pYM10, pYM11 and pYM12, respectively, see Table 2) demonstrated a 5- to 8-fold increase in the number of pMS116 copies in *M. smegmatis* harboring a RepA-encoding plasmid relative to the copy number in *M. smegmatis* harboring a control (pMV361) plasmid (FIG. 10). The increased plasmid copy number correlated with a dramatic increase in the intensity of mycobacterial-promoter-driven GFP expression as measured by flow cytometry (FIGS. 11, 12).

Remarkably, high-plasmid-copy-number *M. smegmatis* strains transferred genes to mammalian cells upon infection at a 3-4-fold higher efficiency than control low-plasmid-copy-number strains. In conclusion, mycobacteria harboring a higher copy number plasmid system may transfer genes more efficiently to mammalian cells. Introducing a high-copy-number system into hyperconjugative mutants of mycobacteria may further enhance the efficiency of gene transfer from mycobacteria to mammalian cells. These modalities may pave the way for novel methods of gene immunization or gene therapy using recombinant mycobacterial vectors.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

```
                           SEQUENCE LISTING

<160> NUMBER OF SEQ ID NOS: 2

<210> SEQ ID NO 1
<211> LENGTH: 24
<212> TYPE: DNA
<213> ORGANISM: Homo sapiens

<400> SEQUENCE: 1
aaaaaaacgc gtgccatccg tggc                                              24

<210> SEQ ID NO 2
<211> LENGTH: 24
<212> TYPE: DNA
<213> ORGANISM: Homo sapiens

<400> SEQUENCE: 2
gctgttacgc gtgtaagcag acag                                              24
```

TABLE 3

List of constructs used to investigate copy number control in this work

| Plasmid | Characteristics | Reference |
| --- | --- | --- |
| pMV261 | oriE, oriM, aph | Stover et al., 2001 |
| pMV361 | oriE, int, aph | Stover et al., 2001 |
| pMS116 | oriE, oriM, hygro, hsp60-eGFP | This work |
| pYM10 | pMV361 with hsp60 promoter-driven repA and RepB | This work |
| pYM11 | pMV361 with hsp60 promoter-driven repA | This work |
| pYM12 | pMV361 with hsp60 promoter-driven RepB | This work |
| CMV-GFP | oriE, oriM, hygro, CMV-eGFP | This work |

What is claimed is:

1. A mycobacterium comprising a recombinant gene operably linked to a mammalian promoter that directs expression of the recombinant gene from a mammalian cell, wherein the mycobacterium is *M. smegmatis* or *M. bovis* BCG, and wherein the mycobacterium overexpresses (i) RepA, (ii) RepB or (iii) RepA and RepB.

2. The mycobacterium of claim 1, wherein the mycobacterium is *M. bovis* BCG.

3. The mycobacterium of claim 1, wherein the mycobacterium is *M. smegmatis*.

4. The mycobacterium of claim 1, wherein the mycobacterium overexpresses RepA.

5. The mycobacterium of claim 1, wherein the mycobacterium overexpresses RepB.

6. The mycobacterium of claim 1, wherein the mycobacterium overexpresses RepA and RepB.

7. The mycobacterium of claim 1, wherein the mycobacterium is capable of hyperconjugation.

8. The mycobacterium of claim 1, wherein the promoter is a human cytomegalovirus immediate-early promoter.

9. The mycobacterium of claim 1, wherein the gene encodes a protein.

10. The mycobacterium of claim 9, wherein the protein is an antigen of a human pathogen.

11. The mycobacterium of claim 10, wherein the human pathogen is influenza.

12. The mycobacterium of claim 1, wherein the gene is on a mycobacterial plasmid.

13. A mammalian cell comprising the recombinant mycobacterium of claim 1.

14. The cell of claim 13, wherein the mycobacterium is *M. bovis* BCG.

15. The cell of claim 13, wherein the mycobacterium is *M. smegmatis*.

16. The cell of claim 13, wherein the mycobacterium overexpresses RepA.

17. The cell of claim 13, wherein the mycobacterium overexpresses RepB.

18. The cell of claim 13, wherein the mycobacterium overexpresses RepA and RepB.

19. A mycobacterial plasmid capable of replication in a mycobacterium, wherein the plasmid comprises a recombinant gene operably liked to a mammalian promoter that directs expression of the recombinant gene from a mammalian cell, wherein the mycobacterium is *M. smegmatis* or *M. bovis* BCG, and wherein the mycobacterial plasmid directs overexpression of (i) RepA, (ii) RepB or (iii) RepA and RepB.

20. The plasmid of claim 19, wherein the mycobacterium is *M. bovis* BCG.

21. The plasmid of claim 19, wherein the mycobacterium is *M. smegmatis*.

22. The plasmid of claim 19, which directs overexpression of RepA.

23. The plasmid of claim 19, which directs overexpression of RepB.

24. The plasmid of claim 19, which directs overexpression of RepA and RepB.

25. A method of expressing a recombinant gene in a mammalian cell, the method comprising infecting the cell with the mycobacterium of claim 1.

26. The method of claim 25, wherein the mycobacterium is *M. bovis* BCG.

27. The method of claim 25, wherein the mycobacterium is *M. smegmatis*.

28. The method of claim 25, wherein the mycobacterium overexpresses RepA.

29. The method of claim 25, wherein the mycobacterium overexpresses RepB.

30. The method of claim 25, wherein the mycobacterium overexpresses RepA and RepB.

31. The method of claim 25, wherein the gene encodes an antigen of a human pathogen.

* * * * *

UNITED STATES PATENT AND TRADEMARK OFFICE
CERTIFICATE OF CORRECTION

PATENT NO. : 7,939,089 B2  
APPLICATION NO. : 11/794372  
DATED : May 10, 2011  
INVENTOR(S) : Jacobs, Jr. et al.

Page 1 of 1

It is certified that error appears in the above-identified patent and that said Letters Patent is hereby corrected as shown below:

In the Specifications

Column 1, line 17, "Grant No. R21 EB002857" should be changed to

--Grant Nos. R21 EB002857 and R21 EB004165--

Signed and Sealed this  
Seventh Day of January, 2014

Margaret A. Focarino  
*Commissioner for Patents of the United States Patent and Trademark Office*